US008513311B2

(12) United States Patent
Sagalowicz et al.

(10) Patent No.: US 8,513,311 B2
(45) Date of Patent: *Aug. 20, 2013

(54) OIL-IN-WATER EMULSION AND ITS USE FOR THE DELIVERY OF FUNCTIONALITY

(75) Inventors: Laurent Sagalowicz, Cully (CH); Martin Leser, Bretigny (CH); Martin Michel, Lausanne (CH); Heribert Johann Watzke, Lausanne (CH); Simone Acquistapace, La Tour-de-Peilz (CH); Raymond Bertholet, Blonay (CH); Birgit Holst, Bulgneville (FR); Fabien Robert, Divonne les Bains (FR)

(73) Assignee: Nestec S.A., Vevey (CH)

( * ) Notice: Subject to any disclaimer, the term of this patent is extended or adjusted under 35 U.S.C. 154(b) by 1438 days.

This patent is subject to a terminal disclaimer.

(21) Appl. No.: 12/093,560

(22) PCT Filed: Nov. 22, 2006

(86) PCT No.: PCT/EP2006/068761
§ 371 (c)(1),
(2), (4) Date: May 13, 2008

(87) PCT Pub. No.: WO2007/060177
PCT Pub. Date: May 31, 2007

(65) Prior Publication Data
US 2008/0255247 A1    Oct. 16, 2008

(30) Foreign Application Priority Data
Nov. 22, 2005  (EP) .................................. 05025439

(51) Int. Cl.
*A23L 1/00* (2006.01)
*A23G 3/32* (2006.01)
(52) U.S. Cl.
USPC ............... 514/772; 516/53; 426/89; 426/103; 435/252.1; 512/4
(58) Field of Classification Search
USPC ............... 516/53; 514/772; 512/4; 426/89, 426/103; 435/252.1
See application file for complete search history.

(56) References Cited

U.S. PATENT DOCUMENTS

| | | | | |
|---|---|---|---|---|
| 4,933,192 | A | * | 6/1990 | Darling et al. .................. 426/98 |
| 5,753,241 | A | | 5/1998 | Ribier et al. |
| 2003/0114352 | A1 | * | 6/2003 | Eh et al. ......................... 512/27 |
| 2004/0022861 | A1 | * | 2/2004 | Williams et al. .............. 424/489 |
| 2004/0101613 | A1 | * | 5/2004 | Levi .............................. 426/601 |

FOREIGN PATENT DOCUMENTS

| | | |
|---|---|---|
| CN | 1953735 | 4/2007 |
| EP | 1 597 973 | 11/2005 |
| EP | 1116515 | 11/2005 |
| EP | 1597973 | 11/2005 |
| EP | 1598060 | 11/2005 |
| EP | 1598060 A1 * | 11/2005 |
| JP | 2004-008837 * | 1/2004 |
| JP | 2004008837 | 1/2004 |
| WO | WO 9963841 | 12/1999 |
| WO | WO 0059475 | 10/2000 |
| WO | 0243698 | 6/2002 |
| WO | WO 02076441 | 10/2002 |
| WO | 03/105607 | 12/2003 |
| WO | 2005004843 | 1/2005 |
| WO | 2005014162 | 2/2005 |
| WO | 2005110370 | 11/2005 |
| WO | WO 2005/110370 * | 11/2005 |
| WO | 2007060171 | 5/2007 |

OTHER PUBLICATIONS

Nakano et al., "Dispersions of liquid crystalline phases of the monoolein/oleic acid/pluronic F127 system," Langmuir American Chemical Society, vol. 18, 2002, pp. 9283-9288, XP002344327, ISSN: 0743-7463.
Gustafsson et al., "Submicron particles of reversed lipid phases in water stabilized by a nonionic amphiphilic polymer," Langmuir, American Chemical Society, vol. 17, 2001, pp. 3917-3922, XP002344326, ISSN: 0743-7463.
Nakano et al., "Small angle X-ray Scattering and 13-C NMR investigation on the Internal Structure of Cubosomes," Langmuir, American Chemical Society, vol. 17, 2001, pp. 3917-3922, XP002344325.
Monduzzi et al., "A 13-C NMR Study of Aqueous Dispersions of Reversed Lipid Phases," Langmuir, American Chemical Society, vol. 16, 2000, pp. 7355-7358, XP002344324, ISSN: 0743-7463.
R. Ostlund et al., "Sitostanol administered in lecithin micelles potently reduces cholesterol absorption in humans," Am. J. Clin. Nutr., 1999, vol. 70, pp. 826-831.
M. Kinoshita et al., "Improvement of solubility and oral bioavailability of a poorly water-soluble drug, TAS-201, by its melt absorption on a porous calcium silicate," Journal of Pharmaceutical Sciences, vol. 91 (2), pp. 362-370. Published online Jan. 8, 2002.

(Continued)

Primary Examiner — Ling Choi
Assistant Examiner — Chun-Cheng Wang
(74) Attorney, Agent, or Firm — K&L Gates LLP

(57) ABSTRACT

The present invention concerns an oil-in-water emulsion wherein the oil droplets of a diameter in the range of 5 nm to hundreds of micrometers exhibit a nano-sized self-assembled structurization with hydrophilic domains having a diameter size in the range of 0.5 to 200 nm, due to the presence of a lipophilic additive and the oil-in-water emulsion contains an active element being present in the range comprised between 0.00001 and 79% based on the total composition.

3 Claims, 15 Drawing Sheets

(56) References Cited

OTHER PUBLICATIONS

N. Garti et al., "Current Opinion in Colloid & Interface Science", 1998, vol. 3, pp. 657-667.

B. Binks, "Relationship between Microemulsion Phase Behavior and Macroemulsion Type in Systems Containing Nonionic Surfactant," Langmuir, (1993), vol. 9, pp. 25-28.

P. Izquierdo et al., "Formation and Stability of Nano-emulsions Prepared Using the Phase Inversion Temperature Method," Langmuir, (2002), vol. 18, pp. 26-30.

W.D Bancroft, "The Theory of Emulsification," J. Phys. Chem (1913) 17, p. 501-519.

International Search Report for International Application No. PCT/EP2006/068761 mailed Feb. 21, 2007.

Written Opinion for International Application No. PCT/EP2006/068761 mailed Feb. 21, 2007.

Leser et al., "Self-assembly of polar food lipids," Advances in Colloid and Interface Science, vol. 123-126 (2006), pp. 125-136.

Anan Yaghmur et al., "Emulsified Microemulsions and Oil-Containing Liquid Crystalline Phases", 2005 American Chemical Society, pp. 568-577.

* cited by examiner

OIL-IN-WATER EMULSION AND ITS USE FOR THE DELIVERY OF FUNCTIONALITY

FIELD OF INVENTION

The present invention concerns an oil-in-water emulsion in which the dispersed oil droplets exhibit a self assembled structure, that is used to solubilize or disperse active elements, such as nutrients, drugs, aromas or chemicals, in order to deliver a new or improved functionality.

BACKGROUND OF THE INVENTION

Emulsions in Industry

Emulsions are common colloidal systems in many industrial products such as Food, Cosmetics, Pharmaceutical or Agrochemical preparations. They are often used to deliver functional molecules, or to create a certain texture or pleasure to the consumer. Oil-in-water emulsions are made of oil droplets which are dispersed in an aqueous continuous phase. The dispersed oil droplets are stabilised by hydrophilic surface active molecules which form a layer around the oil droplets. In order to disperse the oil phase into the continuous aqueous phase, homogenisers are used which enable to produce oil droplets in various size ranges (having a radius from ca 100 nm up to several hundreds of micrometers). The formation of the layer around the oil droplets during the homogenisation step renders the oil droplets kinetically stable against coalescence, flocculation or coagulation.

The surface active material used in oil-in-water based emulsion products can either be low molecular weight hydrophilic surfactants, such as polysorbates, lysolecithins etc, or polymers, such as proteins, e.g. gelatin or proteins from milk, soya, or polysaccharides, such as gum arabic or xanthan or particulated materials, such as silica particles, or mixtures thereof.

Oil-in-water emulsion based products are ubiquitous in—Food, Cosmetics, Pharmaceuticals or Agro-chemicals. Prominent oil-in-water emulsion-based food products are for instance milk, mayonnaise, salad dressings, or sauces. Prominent oil-in-water emulsion-based products used in the cosmetical or pharmaceutical Industry are lotions, creams, milks, pills, tablets etc. The oil droplets in such products are usually made of, for instance, triglycerides, diglycerides, waxes, fatty acid esters, fatty acids, alcohols, mineral oils, hydrocarbons, or other oily substances.

Emulsions are used either as a starting material, intermediate or final product or as an additive to a final product.

Emulsions for Delivery of Active Elements

One of the uses of emulsions in Industry is to deliver active compounds, such as, flavours, vitamins, antioxidants, neutraceuticals, phytochemicals, drugs, chemicals, etc. Administrating of the active components requires the use of an appropriate vehicle for bringing an effective amount of the active component into the desired place of action. Oil-in-water emulsions are commonly used delivery systems since they take advantage of the increased solubility of lipophilic active compounds in the oil. In EP 1116515, as an example of using emulsions for controlling flavour performance, a hydrophobic active ingredient, such as a flavour component, is mixed into a matrix via an extruder in form of an oil-in-water emulsion in order to increase the stability of the introduced active ingredient during further processing of the product. In WO 00/59475, as an example for a pharmaceutical oil-in-water emulsion, a composition and method for improved delivery of ionizable hydrophobic therapeutic agents is described, which are mixed together with an ionizing agent, a surfactant and a triglyceride to form an oil-in-water emulsion. WO 99/63841, as an example for the use of emulsions in the food area, describes compositions comprising phytosterol having enhanced solubility and dispersibility in an aqueous phase due to the formation of an emulsion or a microemulsion.

Dissolution of active elements, such as phytosterols, lycopene or water-insoluble drugs into the oil droplets of o/w emulsions or dispersions cannot only facilitate the dispersibility, i.e. the homogeneous incorporation of the active elements into the product, but can also be used to increase their bioaccessibility or bioavailability. Clinical and animal experiments showed that the maximum efficiency and bioavailability of active elements, such as drugs and nutrients, is, in general, obtained when the active elements are solubilized or dissolved, for instance into micelles, and not present in the form of large crystals (Ostlund, E. O., C. A. Spilbourg, et al. (1999). "Sitostanol adminstered in lecithin micelles potently reduces cholesterol absorption in humans." *American Journal of Clinical Nutrition* 70: 826-31; M. Kinoshita, K. Baba, et al. (2002). "Improvement of solubility and oral bioavailability of a poorly water-soluble drug, TAS-301, by its melt adsorption on a porous calcium silicate." *Journal of Pharmaceutical Sciences* 91(2): 362-370). Small or micronized crystals are more likely to be bioavailable than large ones since they will faster dissolve during digestion.

If the oil droplets in the oil-in-water emulsions are ultra small, e.g. in the order of several nanometers to about 200 nm diameter, the emulsion is called oil-in-water microemulsion (Evans, D. F.; Wennerström, H. (Eds.); 'The Colloidal Domain', Wiley-VCH, New York, (1999)). These emulsions are clear and thermodynamically stable and, therefore, are for the man skilled in the art different from ordinary emulsions the latter being thermodynamically unstable and generally turbid.

DESCRIPTION OF THE INVENTION

As state of the art, dispersed oil droplets in oil-in-water emulsions are used as vehicles for lipophilic molecules which are dissolved in the oil droplets. The drawback of this kind of emulsions as a vehicle system is that they are not able to host crystallinic (i.e. present in a crystalline form), hydrophilic or amphiphilic molecules alone or in combination with lipophilic compounds due to the lack of molecular solubility in the oil phase. Especially difficult is the delivery of crystallinic or amphiphilic or hydrotrope compounds because of their tendency to disturb the stabilizing function of the hydrophilic emulsifiers, and, as a consequence, they can destabilize the emulsion.

The present invention is based on the finding of novel nano-sized self-assembled structures in the interior of ordinary oil droplets that can accumulate both lipophilic, amphiphilic and hydrophilic molecules. The structures are formed by the addition of a lipophilic additive (denoted as LPA) to the oil droplets. Such structures can solubilize not only lipophilic components but also in the same time hydrophilic and/or amphiphilic or hydrotropic or crystallinic components. The nano-sized self-assembled structures inside the oil droplets mainly consist of nano-sized and thermodynamically stable hydrophilic domains, i.e., water droplets, rods or channels. The nano-sized domains, which are formed spontaneously (thermodynamically driven) inside the emulsion oil droplets, are stabilized by the LPA. The hydrophilic part of the LPA molecule is part of the hydrophilic domain structure. The hydrophilic domains can be of the size of 0.5 to 200 nm of diameter. Preferably the hydrophilic domain is in the range of 0.5 to 150 nm of diameter. Even more preferably the hydrophilic domain is in the range of 0.5 to 100 nm of diameter. And most preferably the hydrophilic domain is in the range of 0.5 to 50 nm.

As used herein, the 'hydrophilic domain' consists of the water domains and the hydrophilic headgroup area of the LPA molecules. Due to the ultra-small size of the hydrophilic domains, they also exhibit a large surface area which is a suitable location for the solubilization of a variety of different active elements.

The invention is directed to the delivery of lipophilic, and/or crystallinic, and/or amphiphilic active elements, which will be localised inside the LPA chain regions in the oil droplets. Moreover, the invention is directed to the delivery of hydrophilic or amphiphilic active elements, which are localised in the headgroup area of the hydrophilic domains inside the oil droplets or in the hydrophilic domains inside the oil droplets or in the aqueous phase outside the oil droplets. The presence of the large surface area inside the oil droplets allows creating new or improved functionalities, which are not possible to create in the absence of the surface area or hydrophilic domains inside the oil droplets of the oil-in-water emulsion. For examples solubilization or association of active elements into these self-assembly structures in the oil droplets lead to different functionalities. The present invention concerns further the oil-in-water emulsion described above for the following uses:

- Enhanced solubility or/and dispersibility of water insoluble, oil insoluble active elements, crystallinic active elements due to the presence of the nano-sized self-assembled structure inside the oil droplets. The active elements would crystallise out at the temperature of use or storage when dissolved in ordinary oil-in-water emulsions.
- Enhanced stability, protection against chemical degradation or oxidation of active elements in the oil-in-water emulsion due to the formation of the nano-sized self-assembled structure inside the oil droplets.
- Enhanced bioavailability, bioaccessibility, biodisponibility, or absorption of active elements during digestion due to the formation of the nano-sized self-assembled structure inside the oil droplets.
- Controlled release, burst release, or sustained release of active elements during consumption or digestion to create or improve a functionality acting on the health due to the formation of the nano-sized self-assembled structure inside the oil droplets.
- Increased efficiency of an active element, sustained efficiency of an active element, or burst release of an active element to add or improve a functionality acting on the health due to the formation of the nano-sized self-assembled structure inside the oil droplets.
- Controlled release of aroma or flavour, burst release of aroma or flavour, or sustained release of aroma or flavour to create new or improved sensory properties due to the formation of the nano-sized self-assembled structure inside the oil droplets.
- Creation of different taste, different texture, mouth feel, mouth coating, or creaminess sensation due to the formation of the nano-sized self-assembled structure inside the oil droplets.
- Taste or off taste masking of an active element due to the formation of the nano-sized self-assembled structure inside the oil droplets.
- Flavour or off flavour masking of an active element, of a structure, etc due to the formation of the nano-sized self-assembled structure inside the oil droplets.
- Taste or flavour modulation of an active element due to the formation of the nano-sized self-assembled structure inside the oil droplets.
- Colour modulation or increased browning via Maillard reaction due to the formation of the nano-sized self-assembled structure inside the oil droplets.
- Colour modulation, increased browning, increased chemical reaction or Maillard reaction yield during heating or microwave action due to the formation of the nano-sized self-assembled structure inside the oil droplets.
- Control of chemical reaction yield or control of Maillard reaction yield due to the formation of the nano-sized self-assembled structure inside the oil droplets.
- Control of chemical reaction yield or control of Maillard reaction yield during heating or microwave action due to the formation of the nano-sized self-assembled structure inside the oil droplets.
- Extraction of active elements from any kind of raw materials or products for enrichment of active elements in the oil-in-water emulsion due to the formation of the nano-sized self-assembled structure inside the oil droplets.
- Extraction of active elements from raw materials or products, in the mouth, during consumption, mastication or digestion in order to control their release for health or sensory benefits due to the formation of the nano-sized self-assembled structure inside the oil droplets.
- Any kind of functionality which is based on a combination of the above described functionalities due to the formation of the nano-sized self-assembled structure inside the oil droplets.
- Any kind of functionality or combination of functionalities described above which is obtained by changing the internal structure of the oil-in-water emulsion droplets or changing the structure of the whole oil-in-water emulsion during heating, cooling, processing, mastication, consumption or digestion or in the mouth due to the formation of the nano-sized self-assembled structure inside the oil droplets.

The presence of an active element in the oil-in-water emulsion of this invention brings new or improved functionality to the product. Example of active elements are flavors, flavor precursors, aromas, aroma precursors, taste enhancers, salts, sugars, amino-acids, polysaccharides, enzymes, peptides, proteins or carbohydrates, food supplements, food additives, hormones, bacteria, plant extracts, medicaments, drugs, nutrients, chemicals for agro-chemical or cosmetical applications, carotenoids, vitamins, antioxydants or nutraceuticals selected from the group comprising of lutein, lutein esters, β-carotene, tocopherol, tocopherol acetate, tocotrienol, lycopene, Co-$Q_{10}$, flax seed oil, fish oil, omega-3 oils, omega-6 oils, DHA, EPA, arachidonic-rich oils, LCPUFA oils, menthol, mint oil, lipoic acid, vitamins, polyphenols and their glycosides, ester and/or sulfate conjugates, isoflavones, flavonols, flavanones and their glycosides such as hesperidin, flavan 3-ols comprising catechin monomers and their gallate esters such as epigallocatechin gallate and their procyanidin oligomers, vitamin C, vitamin C palmitate, vitamin A, vitamin $B_{12}$, vitamin D, α- and/or γ-polyunsaturated fatty acids, phytosterols, esterified phytosterols, free, non esterified phytosterols, zeaxanthine, caffeine, and a combination thereof.

The active element can be an oil, a LPA, water soluble, water insoluble, oil soluble or oil insoluble.

The active element can be directly added to the emulsion to deliver a new or improved functionality to the product. Such active elements can be, for example, drugs, nutrients, aromas or flavours. The active element can also indirectly deliver new or improved functionalities to the product. For example, addition of a lipophilic additive, such as a monoglyceride or a phospholipid, changes the internal nano-structure of the oil droplets. A change of the internal nano-structure of the oil droplet will allow inducing new or improved functionalities, such as a better mouth feel, mouth coating, texture or stability to the product.

An example of an indirectly delivered functionality to the product concerns the physical stability of the oil-in-water emulsion of this invention against creaming, coalescence or flocculation. Addition of a LPA to the dispersed oil droplets significantly improves the physical stability of the emulsion against creaming and coalescence when compared to ordinary emulsion formulations (no LPA added to the oil droplet phase; reference emulsion). Addition of a LPA to the oil droplets, i.e., generating hydrophilic domains inside the oil droplets (containing a certain amount of water), increases the specific weight of the emulsion droplets and, hence, decreases the creaming rate or even stops creaming of the droplets, and avoids the formation of a 'ring' at the top of the emulsion. Ring formation is a typical result of an extensive creaming.

The emulsion systems of this invention are clearly distinguished from emulsions commonly known as water-oil-water double emulsions. w/o/w (water/oil/water) double emulsions are oil-in-water emulsions, in which the oil droplets contain micron-sized water droplets (Garti, N.; Bisperink, C.; Curr. Opinion in Colloid & Interface Science (1998), 3, 657-667). The water droplets inside the dispersed double emulsion oil droplets are prepared (dispersed) by mechanical energy input, e.g., homogenisation, and, as a consequence, are thermodynamically unstable and not self-assembled. The diameter of the inner water droplets in a w/o/w double emulsion is larger than 300 nm diameter. The emulsions of this invention can easily be distinguished from ordinary w/o/w double emulsions since the formation of the nano-sized self-assembled structure inside the oil droplets of the emulsion of this invention is spontaneous and thermodynamically driven, and the mean diameter of the water droplets or channels is below 200 nm.

Thus the invention is directed towards oil droplets which contain a nano-sized self-assembled structure with hydrophilic domains, in the range of 0.5 nm to 200 nm, and the oil droplets or the oil-in-water emulsion of this invention contain an active element. The amount of the active element is higher than 0.00001% of the total composition. Preferably it is higher than 0.00003%, more preferably higher than 0.0001%. And even more preferably the amount of the active element is higher than 0.001% of the total composition. The amount of active element is comprised between 0.00001 and 79%. It is also possible to have an amount of active element comprised between 0.00001 and 50%. The amount of the active element can also be comprised between 0.001 and 10%. The amount of the active element is lower than 79%. Preferably the amount of active element is lower than 50% based on the total composition. Any combination of the lower and upper range is comprised in the scope of the present invention. The amount of the active element can be given in wt % or mol %.

The notion 'self-assembly' or 'self-organization' refers to the spontaneous formation of aggregates (associates) or nano-structures by separate molecules. Molecules in self-assembled structures find their appropriate location based solely on their structural and chemical properties due to given intermolecular forces, such as hydrophobic, hydration or electrostatic forces (Evans, D. F.; Wennerström, H. (Eds.); 'The Colloidal Domain', Wiley-VCH, New York, (1999)). The result of self-assembly does not depend on the process of preparation itself and corresponds to a state of minimum energy (stable equilibrium) of the system.

JP 2004 008837 discloses an oil in water emulsion which contains water-soluble solid particles present in the oil droplets. The particles are in the size range of 20 nm to 10 µm. The particles are prepared in a water-in-oil (w/o) emulsion by means of dehydration (i.e., not a spontaneous process) before the whole particle/oil (S/O) suspension is dispersed in an aqueous phase using the porous membrane emulsification process.

WO 02/076441 discloses the use of an alcohol-in-fluorcarbon microemulsion as a precursor for the preparation of solid nanoparticles The nanoparticles have a diameter below 200-300 nanometers. Nanoparticle formation is not spontaneous and triggered by cooling the precursor microemulsion below about 35° C., or by evaporating the alcohol in the precursor microemulsion or by diluting the microemulsion with a suitable polar solvent.

US 2004/022861 discloses a w/o/w double emulsion, in which the oil droplets containing an aqueous microscopic water phase containing protein or another hydrophilic agent. The whole double emulsion is sprayed into, for instance, liquid nitrogen via a capillary nozzle for production of protein-loaded microparticles.

All these examples describe the non-spontaneous formation of solid hydrophilic (nano)particles using w/o microemulsions or w/o or w/o/w double emulsions and needing an external trigger for the solidification of the hydrophilic domains inside the oil droplets. After preparation of the (nano)particles they are largely unaffected by environmental factors such as temperature, pH, or external fluid properties. It has to be mentioned that ordinary w/o microemulsions in which the water droplets are not solidified, i.e. fluid, are largely affected by such environmental factors.

Numerous scientific research has shown that the type of emulsion (o/w or w/o) formed by homogenisation of the respective Winsor system (Winsor I (o/w microemulsion plus excess of oil) or Winsor II (w/o microemulsion plus excess of water)) is the same as that formed in the microemulsion phase which is in equilibrium of its excess continuous phase. For instance, emulsification of a w/o microemulsion plus excess water (Winsor II system) gives at sufficiently high surfactant concentrations, i.e., larger than the critical concentration of the surfactant in the oil phase $cµc_{oil}$, a w/o emulsion, the continuous phase of which is itself a w/o microemulsion (B. P. Binks, Langmuir (1993) 9, 25-28). This means that when an ordinary w/o microemulsion is diluted with an aqueous phase the formation of a w/o emulsion is preferred over the formation of an o/w emulsion. Binks et al. (B. P. Binks Langmuir (1993) 9, 25-28) explained this behaviour in terms of the partitioning of the surfactant between the water and oil phase in relation to Bancroft's rule (W. D. Bancroft, J. Phys. Chem. (1913) 17, 501): if the surfactant is accumulated in the oil phase, i.e., better soluble in the oil than in the aqueous phase, the formed type of emulsion is always of the w/o and not the o/w-type. In order to form an o/w emulsion from a w/o microemulsion or a Winsor II system (w/o microemulsion plus excess water), it is necessary that the surfactant undergoes a phase inversion, i.e., a change of its solubility from oil-soluble (formation of the w/o emulsion) to water-soluble (formation of a o/w emulsion) (P. Izquierdo et al., Langmuir (2002) 18, 26-30). Using nonionic surfactants such as alkylethoxylates, e.g. the $C_{12}EO_4$), this can be achieved by cooling the system from 40-50° C. (PIT temperature) down to 25° C. This is completely different from the present invention which correlates the phase behaviour of a lipophilic additive (LPA; forms a w/o microemulsion at room temperature in the oil phase) to the formation of an o/w emulsion in which the oil droplets, containing hydrophilic domains or LPA, are stabilized by an ordinary water-soluble emulsifier. In this case the hydrophilic domains are fluid and not solid. The w/o microemulsion or the oil containing the hydrophilic domains can be diluted (dispersed) in an aqueous phase without undergoing a phase inversion and loosing the hydrophilic domains inside the dispersed oil droplets and without the necessity of solidifying the internal hydrophilic domains in the oil droplets before the dispersion step.

According to the invention, the spontaneous formation of the nano-sized self-assembled structure inside the oil droplets of the oil-in-water emulsion of this invention can be realised in different ways. One way is to add a lipophilic additive (LPA) that allows the spontaneous formation of the nano-sized self-assembled structure, to the oil phase prior to the homogenisation step. The other way is to add the lipophilic additive (LPA) to the emulsion product after the homogenisation step. In this case the lipophilic additive will dissolve into the oil droplets and will lead to the spontaneous formation of the nano-sized self-assembled structure inside the oil droplets. As homogeniser, an ordinary industrial or lab-scale homogeniser, such as a Rannie piston homogeniser, a Kinematica rotor stator mixer, a colloid mill, a Stephan mixer, a Couette shear cell or a membrane emulsification device can be taken. Moreover, ultrasound, steam injection or a kitchen mixer are also suitable to produce the emulsion described in this invention. The spontaneous formation of the nano-sized self-assembled structure inside the oil droplets is independent on the energy intake, used to make the emulsion, and the sequence of LPA addition. This means that also Nano and Microfluidics technics are suitable to make the emulsion of this invention.

Heating may also facilitate the dispersion process since the internal structure at high temperatures may be less viscous and the dispersion process may require less shear forces at higher temperatures than at lower temperatures.

Another route for making the emulsion of this invention is the use of hydrotropes or water structure breakers, or spontaneous emulsification which can be chemically or thermodynamically driven (Evans, D. F.; Wennerström, H. (Eds.); 'The Colloidal Domain', Wiley-VCH, New York, (1999)).

Another route for making the emulsion of this invention is by combining the spontaneous formation of the nano-sized self-assembled structure inside the oil droplets of the oil-in-water emulsion with the spontaneous formation of the oil droplets, i.e., the entire emulsion of this invention, by adding diblock-copolymer or apoprotein-like biopolymers, such as protein-polysaccharide conjugates or coacervates or protein-polysaccharide, protein-protein, or polysaccharide-polysaccharide hybrids or mixtures of polymers or biopolymers or hydrophilic low molecular weight surfactants.

Another route for making the emulsion of this invention is to use dialysis. One way is to mix the lipophilic additive (LPA) to the oil phase and to the hydrophilic emulsifier, used to stabilize the oil droplets in the emulsion. The mixture consisting of the LPA, the oil phase and the hydrophilic emulsifier are mixed with water in such a way that a micellar or lamellar or any other phase is formed. Using a dialysis membrane enables to remove the excess of the hydrophilic emulsifier in the bulk aqueous phase and the oil-in-water emulsion of this invention is formed.

Another route for making the emulsion of this invention is to use the control action of a guest molecule to modify the internal structure of the oil droplets of this invention in such a way that the oil droplet phase is less viscous and requires less energy to be dispersed into the aqueous phase than the droplet phase consisting of the oil-LPA-water and no guest molecule. Dispersing the concentrated mixture (oil-LPA-Guest molecule-water) will be easy since the oil phase structure is of low viscosity. The internal structure of the oil droplets of the emulsion changes upon dilution since guest molecules leaves the oil droplets and dissolves into the aqueous continuous phase during homogenisation and dilution. For this route, the guest molecule is preferably hydrophilic and osmotically active.

Emulsion Formulation

The present invention concerns an oil-in-water emulsion, wherein the oil droplets (having a diameter in the range of 5 nm to hundreds of micrometers) exhibit a nano-sized structurization with hydrophilic domains, in the range 0.5 nm-200 nm, being formed by a lipophilic additive (LPA) and the oil-in-water emulsion contains an active element. The amount of the active element is higher than 0.00001% of the total composition. Preferably it is higher than 0.00003%, more preferably higher than 0.0001%, and even more preferably higher than 0.001% of the total composition. The amount of the active element is comprised between 0.00001 and 79%. It is also possible to have an amount of active element comprised between 0.00001 and 50%. The amount of the active element is lower than 79%. Preferably, the amount of active element is lower than 50% based on the total composition. Any combination of the lower and upper range is comprised in the scope of the present invention. The amount of the active element can be given in wt % or mol %.

The LPA can be added as such or made in-situ by chemical, biochemical, enzymatic or biological means. The amount of oil droplets present in the emulsion of this invention (oil droplet volume fraction) is the amount generally used in ordinary oil-in-water emulsion products. It can vary between 0.00001 wt % and 80 wt %. The oil-in-water emulsion of the invention can be either an oil-in-water emulsion (larger oil droplets), a o/w minie-emulsion, a o/w nano-emulsion or an o/w microemulsion, depending on the size of the oil droplets.

More precisely, the present invention is directed to oil-in-water emulsions comprising dispersed oil droplets having a nano-sized self-assembled structured interior comprising (i) an oil selected from the group consisting of mineral oils, hydrocarbons, vegetable oils, waxes, alcohols, fatty acids, mono-, di- or tri-acylglycerols, essential oils, flavouring oils, lipophilic vitamins, esters, neutraceuticals, terpins, terpenes and mixtures thereof, a lipophilic additive (LPA) or mixtures of lipophilic and hydrophilic additives, having a resulting HLB value (Hydrophilic-Lipophilic Balance) lower than about 10, preferably lower than 8.

(iii) hydrophilic domains in form of droplets, rods or channels comprising of water or a non-aqueous polar liquid, such as a polyol, and an aqueous continuous phase, which contains hydrophilic emulsion emulsifiers.

As used herein, a 'lipophilic additive' (abbreviated also as 'LPA') refers to a lipophilic amphiphilic agent which spontaneously forms stable nano-sized self-assembled structures in a dispersed oil phase. The lipophilic additive (mixture) is selected from the group consisting of fatty acids, sorbitan esters, propylene glycol mono- or diesters, pegylated fatty acids, monoglycerides, derivatives of monoglycerides, diglycerides, pegylated vegetable oils, polyoxyethylene sorbitan esters, phospholipids, cephalins, lipids, sugar esters, sugar ethers, sucrose esters, polyglycerol esters and mixtures thereof.

According to the first embodiment of the invention the oil-in-water emulsion exhibits oil droplets having an internal structure taken from the group consisting of the $L_2$ structure or a combination of a $L_2$ and oil structure (microemulsion or isotropic liquid droplets) in the temperature range of 0° C. to 100° C.

According to the second embodiment of the invention, the oil-in-water emulsion exhibits oil droplets having a $L_2$ structure (microemulsion or isotropic liquid droplets) in the temperature range of 0° C. to 100° C.

According to a third embodiment of the invention, the oil-in-water emulsion exhibits oil droplets having an internal structure taken from the group consisting of the $L_2$ structure (microemulsion or isotropic liquid droplets) or liquid crystalline (LC) structure (e.g. reversed micellar cubic, reversed bicontinuous cubic or reversed hexagonal) and a combination thereof in the temperature range of 0° C. to 100° C.

According to the fourth embodiment of the invention, the oil-in-water emulsion exhibits oil droplets having a LC internal structure in the temperature range of 0° C. to 100° C.

According to a fifth embodiment of the invention, the oil-in-water emulsion exhibits oil droplets having an internal structure taken from the group consisting of the L3 structure, a combination of the L2 and L3 structure, a combination of the lamellar liquid crystalline (L$\alpha$) and L2 structure, and a combination of the lamellar crystalline and L2 structure in the temperature range of 0° C. to 100° C.

According to a sixth embodiment of the invention, the oil-in-water emulsion exhibits oil droplets having an internal structure which is a combination of the previously described structures in the temperature range of 0° C. to 100° C.

All above mentioned internal structures can be without doubt determined by SAXS analysis and by cryo-TEM (Qiu et al. Biomaterials (2000) 21, 223-234, Seddon. Biochimica et Biophysica Acta (1990) 1031, 1-69, Delacroix et al. J. Mol. Biol. (1996) 258, 88-103, Gustafsson et al. Langmuir (1997) 13, 6964-6971, Portes. J. Phys: Condens Matter (1992) 4, 8649-8670) and fast Fourier Transform (FFT) of cryo-TEM images.

For certain applications, the use of temperatures higher than 100° C. (for example retorting temperature or temperature of fusion of crystallinic molecules or temperature of fusion of crystallinic molecules in a media comprising oil or/and LPA) is also possible and is covered by the present invention.

The lipophilic additive (LPA) can also be mixed with a hydrophilic additive (having a HLB larger than 10) up to the amount that the mixture is not exceeding the overall HLB of the mixture of 10 or preferably 8. The additive (mixture) can also be made in-situ by chemical, biochemical, enzymatic or biological means.

The amount of added lipophilic additive is defined as $\alpha$. $\alpha$ is defined as the ratio LPA/(LPA+oil)×100. $\alpha$ is preferably higher than 0.1. More preferably $\alpha$ is higher than 0.5. Even more preferably $\alpha$ is higher than 1. Even more preferably $\alpha$ is higher than 3. Even more preferably $\alpha$ is higher than 10. Most preferably $\alpha$ is higher than 15.

The ratio $\alpha$=LPA/(LPA+oil)*100 is preferably lower than 99.9. More preferably $\alpha$ is lower than 99.5. Even more preferably $\alpha$ is lower than 99.0. Even more preferably $\alpha$ is lower than 95. Even more preferably $\alpha$ is lower than 84. Even more preferably $\alpha$ is lower than 80 and most preferably lower than 70. Any combination of the lower and upper range is comprised in the scope of the present invention. $\alpha$ can be given either in wt-% or mol-%. The lower and higher limit of $\alpha$ depends on the properties of the taken oil and LPA, such as the polarity, the molecular weight, dielectric constant, etc., or physical characteristics such as the critical aggregation concentration (cac) or the critical micellar concentration (cmc) of the LPA in the oil droplet phase.

The emulsion is stabilized by a hydrophilic emulsifier suitable to stabilize ordinary oil-in-water emulsion droplets. The hydrophilic emulsifier can also be denoted "secondary emulsifier" or "stabilizer". The emulsion can be aggregated (flocculated) or not depending on the used hydrophilic emulsifier. The hydrophilic emulsifier is selected from the group consisting of low molecular weight hydrophilic surfactants having a HLB>8, gelatin, proteins from e.g. milk (whey protein isolate, caseinate) or soya, block co-polymers, surface active hydrocolloids such as gum arabic, diblock-copolymer or apoprotein-like biopolymers, such as protein-polysaccaride conjugates or coacervates, or protein-polysaccharide, protein-protein, or polysaccharide-polysaccharide hybrids, conjugates or coacervates or mixtures of polymers and biopolymers. Particles (nano or micro) can also be used to stabilize the oil-in-water emulsion of this invention.

The main consideration of emulsion technologists concerns the selection of surface active ingredients, also denoted as surfactants or emulsifiers, which show good surface properties (or activity), i.e., an effective adsorption to the interface formed around the oil droplets, and an effective and efficient reduction of the interfacial tension. The lower the interfacial tension between the aqueous phase and the oil phase gets, the less energy is needed to increase the water-oil interfacial area, i.e., the easier it is to make smaller oil droplets and more stable emulsions.

Adding a LPA to the oil phase to be emulsified reduces the interfacial tension between the oil phase and pure water. This fact facilitates significantly the break-up of the oil phase of this invention (which contains a certain amount of a lipophilic additive) into small droplets. As a consequence, the break-up process to make the oil-in-water emulsion of this invention does not require effective, highly surface active or quickly adsorbing emulsifiers. The quality (stability, homogeneity) of the formed oil-in-water emulsion of this invention does not depend on the use of efficient and surface active hydrophilic emulsifiers, as used to stabilize ordinary emulsions. 'Badly' adsorbing or wild mixtures of non-efficient emulsifiers, i.e., cheap emulsifier mixtures, are perfectly suitable for the production of stable emulsions of this invention. This means that the role of the hydrophilic emulsifier in the preparation of the oil-in-water emulsion of this invention is mostly to adsorb and wrap around the already broken-up oil droplets and to stabilize them against coalescence. For this purpose, hydrocolloids or other relatively inefficiently adsorbing, slightly amphiphilic polymers, such as carboxymethylcellulose, carrageenan, gellan gum, xanthan gum, galactomannans, protein hydrolysates, peptides, modified starch, etc, or whey protein concentrates, can be also used to stabilize the oil-in-water emulsion of this invention.

The particles (nano or micro) or the outside part of the oil droplet forming the oil-in-water emulsion of the invention can have any kind of internal structure such as amorphous, crystalline, lamellar crystalline, lamellar liquid crystalline, liquid crystalline (LC), L3, L2 or mixture of thereof.

The hydrophilic emulsifier can also be mixed with the LPA, or with the oil, or with the LPA and the oil. This means, that the hydrophilic emulsifier can partly also be present in the interior of the oil droplet and affecting the internal nano-sized self-assembled structure.

The ratio $\beta$=hydrophilic emulsifier/(LPA+oil)×100 describes the amount of hydrophilic emulsifier used to stabilize the oil droplets with respect to the oil plus LPA content. $\beta$ is preferably higher than 0.1. More preferably $\beta$ is higher than 0.5. More preferably β is higher than 1, and more preferably higher than 2. The ratio β=hydrophilic emulsifier/(LPA+oil)×100 is preferably lower than 90. More preferably β is lower than 75. And even more preferably β is lower than 50. Any combination of the lower and upper range is comprised in the scope of the present invention. β can be given either in wt-% or mol-%. In certain cases the hydrophilic emulsifier is added to the formulation. In other cases, the hydrophilic emulsifier can be present in the product itself such as a food product, a cream, etc and in this case, it is not necessary to add it. An example is milk where the proteins already present can be used as hydrophilic emulsifier of the oil-in-water emulsion of this invention.

Various active elements can be solubilized in the nano-sized self-assembled structured interior of the oil droplets. They can be oil-soluble, oil non-soluble, water soluble or crystallinic components selected from the group consisting of flavors, flavor precursors, aromas, aroma precursors, taste enhancers, salts, sugars, amino-acids, polysaccharides, enzymes, peptides, proteins or carbohydrates, food supplements, food additives, hormones, bacteria, plant extracts, medicaments, drugs, nutrients, chemicals for agro-chemical or cosmetical applications, carotenoids, vitamins, antioxydants or nutraceuticals selected from the group comprising of lutein, lutein esters, β-carotene, tocopherol, tocopherol acetate, tocotrienol, lycopene, Co-$Q_{10}$, flax seed oil, fish oil, omega-3 oils, omega-6 oils, DHA, EPA, arachidonic-rich oils, menthol, mint oil, lipoic acid, vitamins, polyphenols and their glycosides, ester and/or sulfate conjugates, isoflavones, flavonols, flavanones and their glycosides such as hesperidin, flavan 3-ols comprising catechin monomers and their gallate esters such as epigallocatechin gallate and their procyanidin oligomers, vitamin C, vitamin C palmitate, vitamin A, vitamin $B_{12}$, vitamin D, α- and γ-polyunsaturated fatty acids, phytosterols, esterified phytosterol, non esterified phytosterol, zeaxanthine, caffeine, and a combination thereof.

In the oil-in-water emulsion according to the invention, the LPA is selected from the group consisting of myristic acid, oleic acid, lauric acid, stearic acid, palmitic acid, PEG 1-4 stearate, PEG 2-4 oleate, PEG-4 dilaurate, PEG-4 dioleate, PEG-4 distearate, PEG-6 dioleate, PEG-6 distearate, PEG-8-dioleate, PEG-3-16 castor oil, PEG 5-10 hydrogenated castor oil, PEG 6-20 corn oil, PEG 6-20 almond oil, PEG-6 olive oil, PEG-6 peanut oil, PEG-6 palm kernel oil, PEG-6 hydrogenated palm kernel oil, PEG-4 capric/caprylic triglyceride, mono, di, tri, tetraesters of vegetable oil and sorbitol, pentaerythrityl di, tetra stearate, isostearate, oleate, caprylate or caprate, polyglyceryl-3 dioleate, stearate, or isostearate, plyglyceryl 4-10 pentaoleate, polyglyceryl 2-4 oleate, stearate, or isostearate, polyglyceryl 4-10 pentaoleate, polyglycewryl-3 dioleate, polyglyceryl-6 dioleate, polyglyceryl-10 trioleate, polyglyceryl-3 distearate propylene glycol mono- or diesters of $C_6$ to $C_{20}$ fatty acid, monoglycerides of $C_6$ to $C_{20}$ fatty acid, lactic acid derivatives of monoglycerides, lactic acid derivatives of diglycerides, diacetyl tartaric ester of monoglycerides, triglycerol monostearate cholesterol, phytosterol, PEG 5-20 soya sterol, PEG-6 sorbitan tetra, hexasterarate, PEG-6 sorbitan tetraoleate, sorbitan monolaurate, sorbitan monopalmitate, sorbitan mono trioleate, sorbitan mono and tristearate, sorbitan monoisostearate, sorbitan sesquioleate, sorbitan sesquistearate, PEG-2-5 oleyl ether, POE 2-4 lauryl ether, PEG-2 cetyl ether, PEG-2 stearyl ether, sucrose distearate, sucrose dipalmitate, ethyl oleate, isopropyl myristate, isopropyl palmitate, ethyl linoleate, isopropyl linoleate, poloxamers, phospholipids, lecithins, cephalins, oat lipids and lipophilic amphiphilic lipids from other plants; and mixtures thereof.

The oil-in-water emulsion according to the invention is normally in liquid or semi-liquid form. According to another embodiment of the invention, the emulsion is dried and is available in powder form. Small angle X-ray scattering and Cryo-TEM show that the internal nano-structure of the oil droplets present in the oil-in-water emulsion of the invention is reconstituted when the dried emulsion is reconstituted by addition of water.

The oil-in-water emulsion according to the invention is either a final product or an additive. The amount of the additive in the final product is not critical and can be varied.

The emulsion, for delivery of functionality, described in this invention is a novel type of emulsion which we name 'ISAMULSION' to describe the specific nature of the oil droplets containing a structure being Internally Self-Assembled, and to exclude the emulsion of this invention from ordinary oil-in-water or w/o/w double emulsions, including nano- and microemulsions, in which the oil droplets do not have a nano-sized self-assembled structure with hydrophilic domains. The ISAMULSION droplets basically consist of oil droplets which have a nano-sized self-assembled structure with hydrophilic domains. This structure can be of a lamellar liquid crystalline, or a lamellar crystalline, or of a reversed nature comprising the L2, the microemulsion, the isotropic liquid phase, the hexagonal, the micellar cubic, or the bicontinuous cubic phase. The structures in the oil phase can appear as a single nano-structure or as a mixture of different nano-structures.

It is excluded from the present invention, the compositions comprising as active element:
   2 wt % R+limonene, 2.6% glycerol monolinoleate and 0.4 wt % Pluronic F127
   10 wt % maltodextrin, 2 wt % d alpha tocopheryl acetate, 2.5 wt % Dimodan U, 0.5 wt % ascorbic acid and 0.375 wt % Pluronic F127
   0.51 wt % soya oil, 2.49 wt % Dimodan U, 0.01 wt % L leucine and 0.2 wt % tween 80
   0.02 wt % soya oil, 2.98 wt % Dimodan U and 0.02 wt % xylose and 0.2 wt % tween 80
   0.51 wt % soybeen oil, 2.49 wt % Dimodan U, 0.03 wt % lyco-mato and 0.2 wt % tween 80
   1.1 wt % soya oil, 0.3 wt % free phytosterol, 1.7 wt % Dimodan U and 0.2 wt % Tween 80

It is, therefore, an object of this invention to provide a new oil-in-water emulsion formulation which can be used for solubilizing active elements in order to deliver a certain number of functionalities.

The present invention concerns the oil-in-water emulsion of the invention for use for enhancing solubility or/and dispersibility of water insoluble, oil insoluble active elements, or crystallinic active elements which crystallise out at the temperature of use or storage using ordinary oil-in-water emulsions.

The invention concerns further the oil-in-water emulsion of the invention for use for enhancing stability, protection against chemical degradation or oxidation of active elements in the oil in water emulsion.

The invention concerns also the oil-in-water emulsion of the invention for use for enhancing bioavailability, bioaccessibility, biodisponibility, or absorption of active elements during digestion.

The invention concerns also the oil-in-water emulsion of the invention for use for controlling release, burst release, or sustained release of active elements during consumption or digestion to create or improve a functionality acting on the health.

The invention concerns also the oil-in-water emulsion of the invention for use for increasing efficiency of an active element, sustained efficiency of an active element, or burst release of an active element to add a functionality acting on the health.

The invention concerns also the oil-in-water emulsion of the invention for use for controlling the release of aroma or flavours or taste, burst release of aroma or flavour, or sustained release of aroma or flavour to create new or improved sensory properties, the aroma or flavour being the active elements.

The invention concerns also the oil-in-water emulsion of the invention for use for creating of different taste, different texture, mouth feel, mouth coating, or creaminess sensation. In this case, the LPA is the active element.

The invention concerns also the oil-in-water emulsion of the invention for use for taste or off taste masking of an active element, for flavour or off flavour masking of an active element, of a structure, taste or flavour modulation of an active element. In this case, the LPA can be itself the active element.

The invention concerns also the oil-in-water emulsion of the invention for use for colour modulation, increased browning via Maillard reaction, increased chemical reaction or Maillard reaction yield during heating or microwave action, control of chemical reaction yield or control of Maillard reaction yield and control of chemical reaction yield or controlled of Maillard reaction yield during heating or microwave action. The active element can be again the LPA.

The invention concerns also the oil-in-water emulsion of the invention for use for extracting of active elements from any kind of raw materials or products for enrichment of active elements in the ISAMULSION, extraction of active elements from raw materials or products, in the mouth, during consumption, mastication or digestion in order to control their release for health or sensory benefits. The active element can be again the LPA itself.

The invention concerns further any kind of functionality which is based on one or a combination of the above described functionalities and any kind of functionality or combination of functionalities described above which is obtained by changing the internal structure of the oil-in-water emulsion droplets or changing the structure of the whole oil-in-water emulsion during heating, cooling, processing, mastication, consumption or digestion in the mouth.

The present invention can be used not only for delivering functionality to food products, but also to products produced in other Industries, such as, Pet Food, Neutraceuticals, Functional Food, Detergents, Nutri-cosmeticals, Cosmetics, Pharmaceuticals, Drug Delivery, Paints, Medical or Agro-chemical Industry, Explosives, Textiles, Mining, Oil well drilling, Paints, Paper Industry, Polymer Industry.

BRIEF DESCRIPTION OF THE DRAWINGS

FIG. 14 represents the remaining percentage of aromas, as measured by head-space measurements, after two days of storage as function of oil droplet structure present in the dispersion (see composition in example 18).

FIG. 1 represents the typical sequence of structures found in the interior of the dispersed oil droplets of the ISAMULSION as a function of the content of the lipophilic additive in % (% LPA=$\alpha=100*LPA/(LPA+OIL)$) and temperature. L2 denotes a reversed microemulsion-like structure; LC denotes the existence of a liquid crystalline phase or a mixture of different liquid crystalline phases. As FIG. 1 shows, a defined nano-sized self-assembled structure is formed at a given temperature and a specific amount of added lipophilic additive ($\alpha$ value) inside the oil droplets (for a closer description of the mentioned structures, see Evans, D. F.; Wennerström, H. (Eds.); 'The Colloidal Domain', Wiley-VCH, New York, (1999)). The amount of added LPA allows to precisely control the type of self-assembly structure, amount of water present in the hydrophilic domains, the amount of internal interface and the size, dimension, of the self-assembly nano-structure formed inside the ISAMULSION droplets. Depending on the oil-type and type of lipophilic additive (LPA), the minimum amount of LPA needed to initiate the spontaneous formation of the self-assembled internal droplet structure is between 0.1 and 5 wt-% on the oil phase.

The internal nano-sized self-assembled structure of the oil droplets in the emulsion can be detected by means of Cryo-TEM or small angle X-ray scattering.

Figure 1:
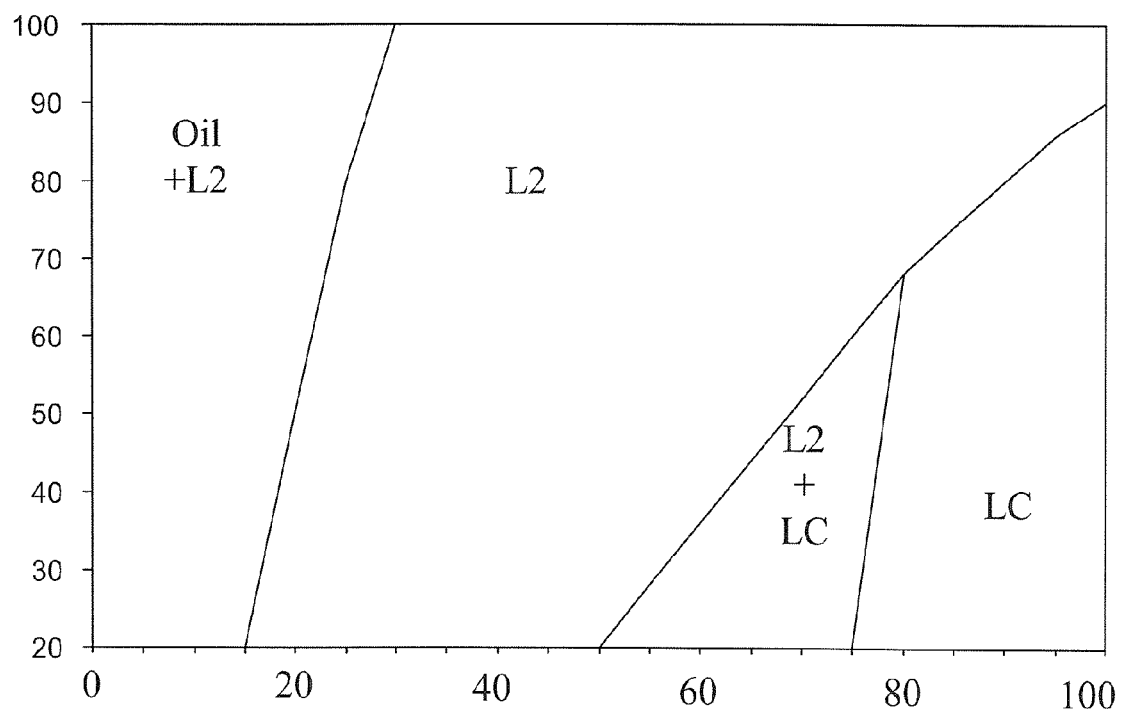
FIG. 1 shows the structure found in the interior of the ISAMULSION oil droplets as a function of $\alpha=100*$ LPA/(LPA+oil)
Figure 2:
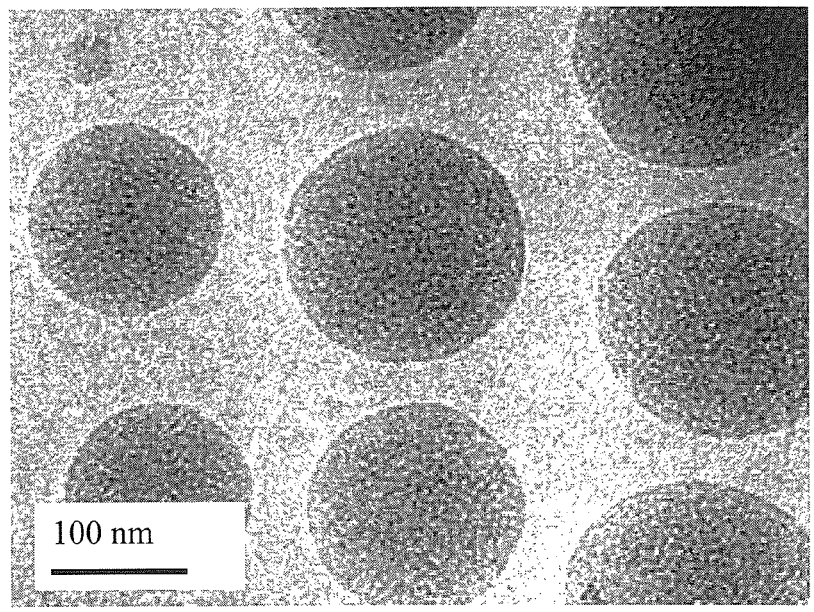
FIG. 2 shows a Cryo-TEM micrograph of a typical ISAMULSION containing oil droplets that have a self-assembly structure with no periodicity.

The cryo-TEM image of FIG. 2 was obtained using the standard technique of Adrian et al (Adrian et al. Nature, (1984) 308, 32-36). A home made guillotine was used for sample freezing. A droplet of 3 μl sample dispersion was deposited onto a copper grid covered with a holy carbon film containing holes of about 2 μm in diameter. A filter paper was pressed on the liquid side of the grid (blotting) for removing excess sample solution.

Figure 6:
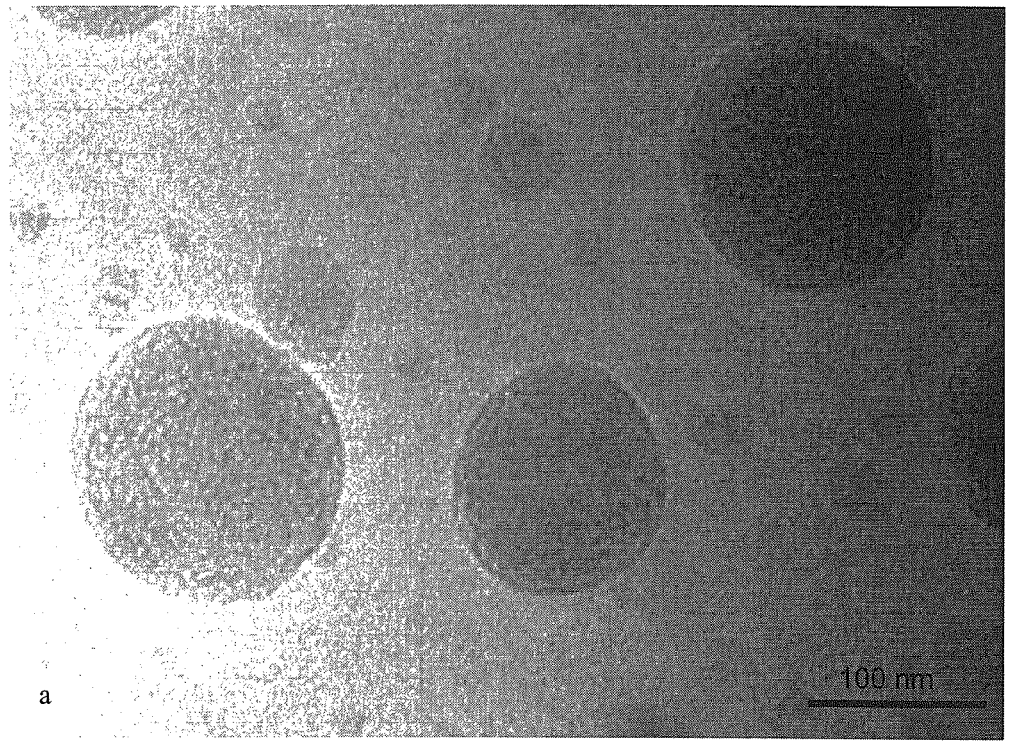
FIG. 6 shows a cryo-TEM image of ISAMULSION oil droplets with no periodic structure (in the presence of a LPA, with nano-structure) (a) in comparison to the corresponding ordinary emulsion droplets (in the absence of a LPA, without nano-structure) (b). Notice that the internal structure that is visible inside the ISAMULSION droplets (FIG. 6a) is invisible in the normal oil droplets (FIG. 6b).
Figure 6:
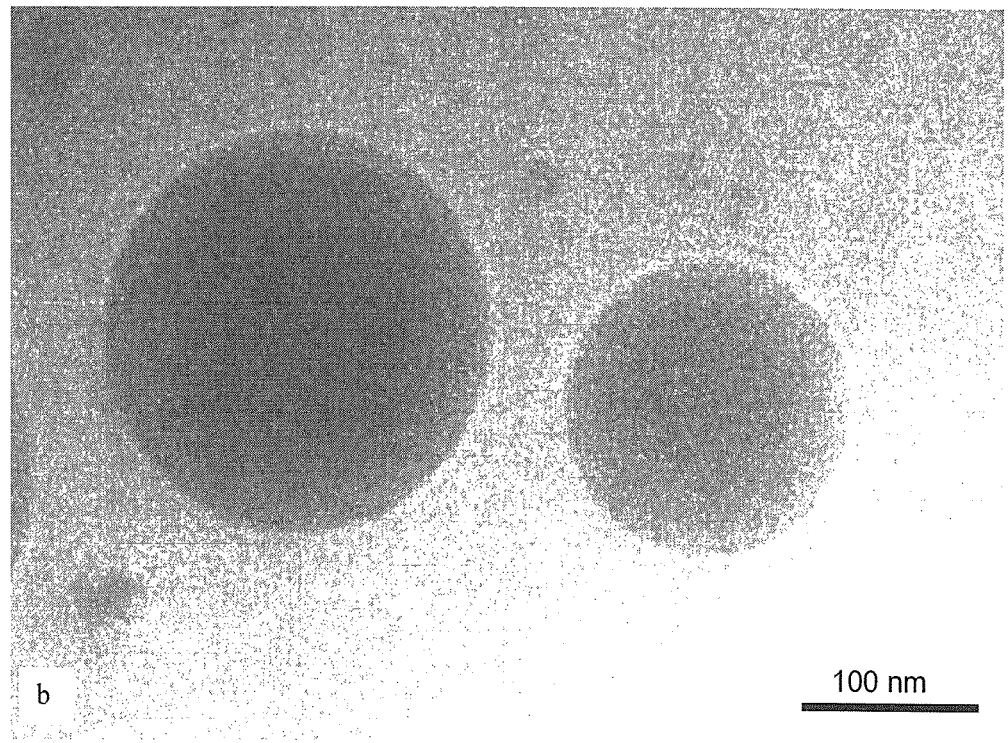
Figure 7:
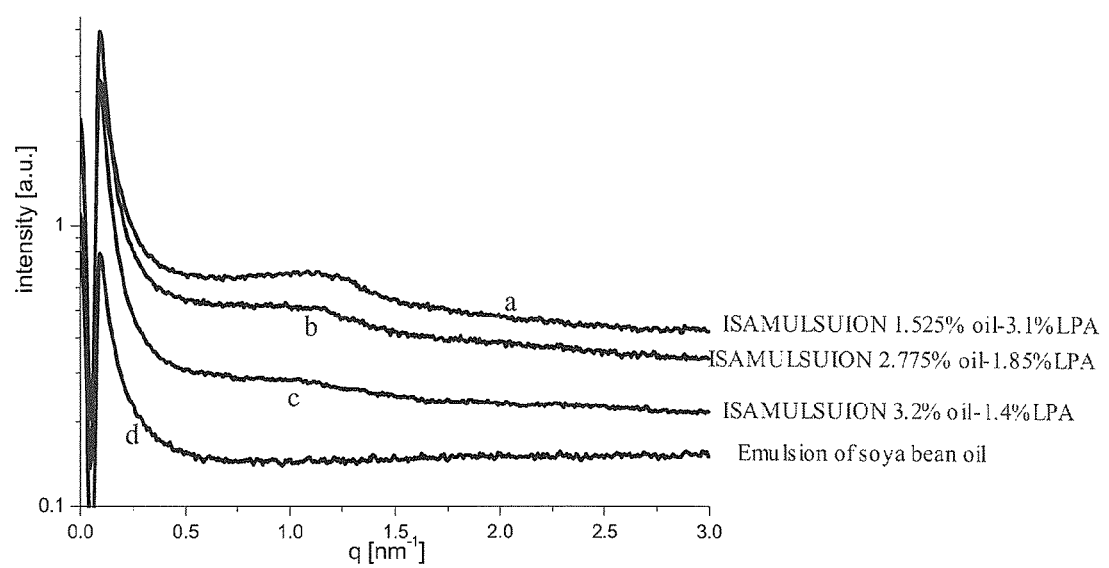
FIG. 7(a) shows the small angle X-ray scattering (SAXS) pattern of the ISAMULSION (with LPA, with nano-structure) and (d) of the corresponding ordinary emulsion (without LPA, without nano-structure). (b) and (c) correspond to ISAMULSIONS with high oil and low LPA content.

Immediately after liquid removal, the grid, held by tweezers, was propelled into liquid ethane. Frozen grids were stored in liquid nitrogen and transferred into a cryo-holder kept at −180° C. Sample analysis was performed in a Philips CM12 TEM at a voltage of 80 kV. Low dose procedures were applied to minimise beam damage. In some cases, a home build environmental chamber similar to the one described by Egelhaaf et al (Egelhaaf et al, J. Microsc. (2000) 200, 128-139) was used. The temperature before thinning and vitrifying was set at 25° C. and 100% humidity was used. The ISAMULSION can be identified by the presence of small bright features inside the oil droplets. FIGS. 2,6a are Cryo-TEM micrographs of ISAMULSIONs, with no periodic structure, showing characteristic distances between the bright features of about 7-8 nm. It should be noted that such bright features are not observed for standard non-structured emulsions and there is no contrast inside non-structured emulsion droplets (FIG. 6b).

Figure 3:
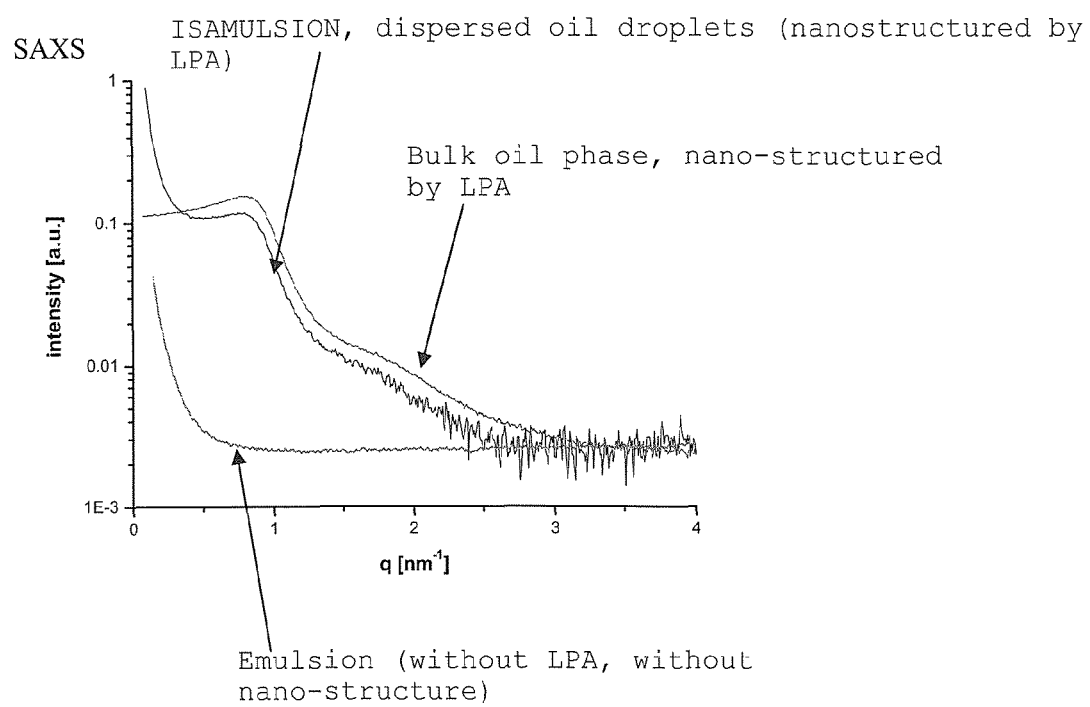
FIG. 3 shows the small angle X-ray scattering (SAXS) pattern of an ISAMULSION, of the bulk oil phase (nano-structured by LPA), which was used for making the ISAMULSION and of the corresponding ordinary emulsion (without LPA, without nano-structure).

The SAXS curves of FIG. 3 were obtained by a standard equipment (Bergmann et al. J. Appl. Cryst. (2000) 33, 869-875), using a X-ray generator (Philips, P W 1730/10) operating at 40 kV and 50 mA with a sealed-tube Cu anode. A Göbbel mirror is used to convert the divergent polychromatic X-ray beam into a focused line-shaped beam of Cu $K_\alpha$ radiation ($\lambda$=0.154 nm). The 2D scattering pattern is recorded by an imaging-plate detector and integrated to the one-dimensional scattering function I(q) using SAXSQuant software (Anton Paar, Graz, Austria), where q is the length of the scattering vector, defined by q=($4\pi/\lambda$)sin $\theta/2$, $\lambda$ being the wavelength and $\theta$ the scattering angle. The broad peaks of scattering profiles were desmeared by fitting these data with the Generalized Indirect Fourier Transformation method (Bergmann et al. (2000), 33, 1212-1216). The characteristic distances are given by d=$2\pi/q$. FIG. 3 shows the small angle X-ray scattering patterns of an ISAMULSION (same as investigated in FIG. 2) together with the corresponding non-dispersed bulk oil phase (nano-structured by LPA) that it is made from, and the corresponding ordinary emulsion (without LPA, without nano-structure). It can be seen that the ISAMULSION shows the same peak position as the non-dispersed bulk oil phase that it is made from. The characteristic distance for both is about 7.5 nm. This characteristic distance is higher than the diameter of the hydrophilic domain. Therefore the hydrophilic domains have a diameter smaller than 7 nm. For the man skilled in the art, this small size of the hydrophilic domains demonstrates that the internal structure of the oil droplet is thermodynamically stable. Moreover, for the corresponding ordinary emulsion, in which no LPA is added (no nano-structure), no peak is observed. This is an additional prove of the presence of a nano-sized self-assembled structure inside the oil droplets of an ISAMULSION. It does not change upon dispersion in water, indicating that the internal ISAMULSION droplet structure is in a thermodynamic equilibrium state.

Figure 5:
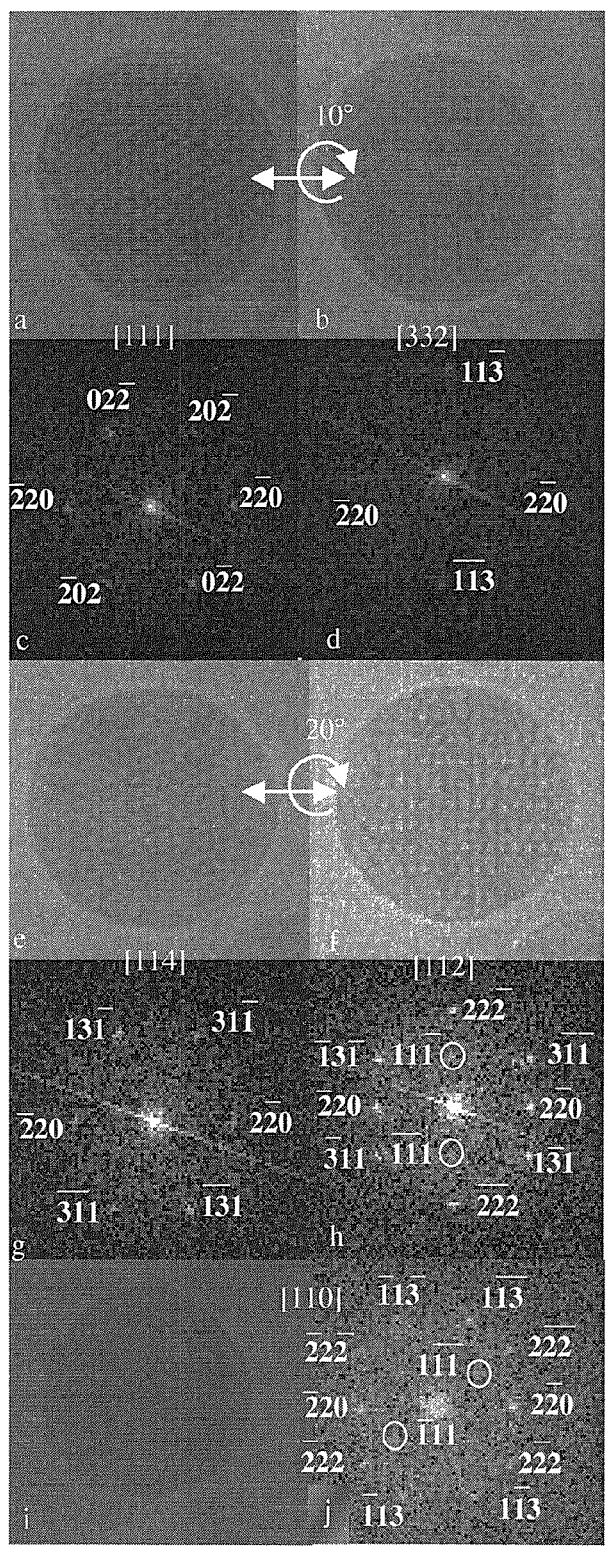
FIG. 5 shows cryo-TEM images of ISAMULSIONs for which the internal structure of oil droplets is micellar cubic and the space group is Fd3m.
Figure 10:
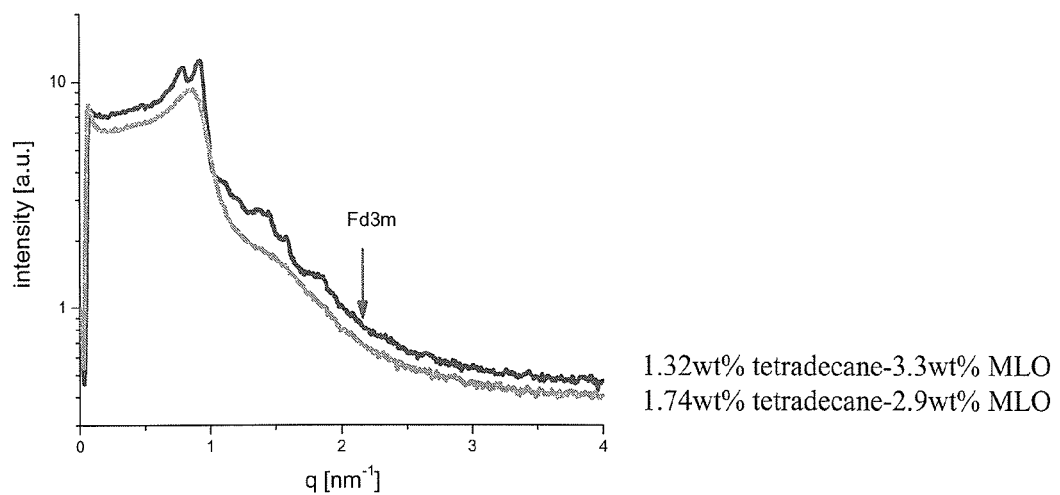
FIG. 10 shows the small angle X-ray scattering (SAXS) pattern of an ISAMULSION containing oil droplets that have an inverse micellar cubic structure.

FIG. 5 shows a cryo-TEM images, with periodic structure inside the oil droplets. Particles are imaged under different directions, and are tilted to go from one direction to another one. Fast Fourier transforms (FFT) are used to determine precisely the planes (or reflections) present and are indexed the same way as indexation of electron diffraction pattern (J. W. Edington, Practical Electron Microscopy in Materials Science, Phillips, Eindhoven, 1974). The particles are observed under the [111] direction (FIG. 5a-c), the [332] direction (FIG. 5b-d), the [114] direction (FIG. 5e-g), the [112] direction (FIG. 5f-h) and the [110] direction (FIG. 5i-j). The first four reflections observed are {111}, {220}, {311} and {222} which identifies the micellar cubic phase (space group Fd3m) as liquid crystalline phase. The same experiments can be done to identify particles with other internal structures. The internal crystallographic structure of particles can also be determined by SAXS as shown in FIG. 10 (micellar cubic, space group Fd3m) and in FIG. 12.

Figure 9:
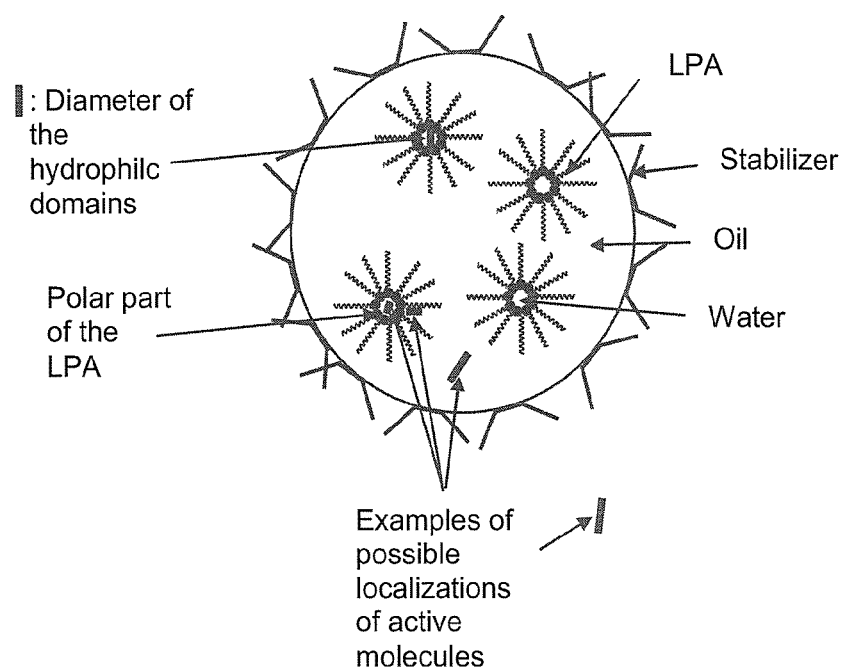
FIG. 9 shows a schematic of an ISAMULSION oil droplet, which contains hydrophilic domains. Note that the hydrophilic domains can be spherical or non-spherical, i.e. rods, disks or channels. Examples of possible localisation of active molecules are shown.

FIG. 9 shows a schematic of an oil droplet which has been nano-structured by addition of a LPA. The structural definition of a hydrophilic domain is specified in FIG. 9. Hydrophilic domains include the polar part (head group) of the LPA (and not the hydrocarbon tail region and the water part). The minimum diameter of a hydrophilic domain can be about 0.5 nm, which is more or less the cross section of 2 head groups containing no water molecules. The minimum size of the polar part of a lipophilic additive or emulsifier is about 0.2 nm. The diameter of a water molecule is about 0.3 nm. The possible localizations of active molecules are shown in FIG. 9.

Figure 13:
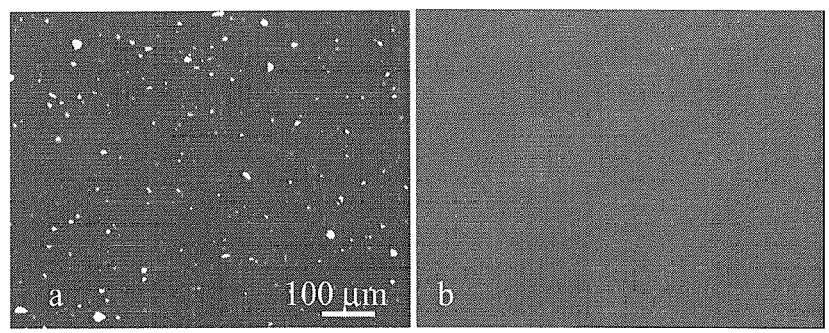
FIG. 13 shows optical microscopy images obtained with Polarized light where: (a) phytosterol crystals are visible when the free phytosterols are present in an oil, and a normal emulsion is formed (b) no phytosterol crystals are present when the free phytosterol is solubilized inside the ISAMULSION droplets.

FIG. 13 shows by polarized light microscopy the presence of crystals when solubilizing free (non esterified) phytosterols in an ordinary emulsion (a), while no crystals are present when phytosterols are solubilized in an ISAMULSION (b). It is well documented that phytosterol in the solubilized form are bioavailable while phytosterol in the crystal form are much less bioacessible and bioavailable.

Figure 14:
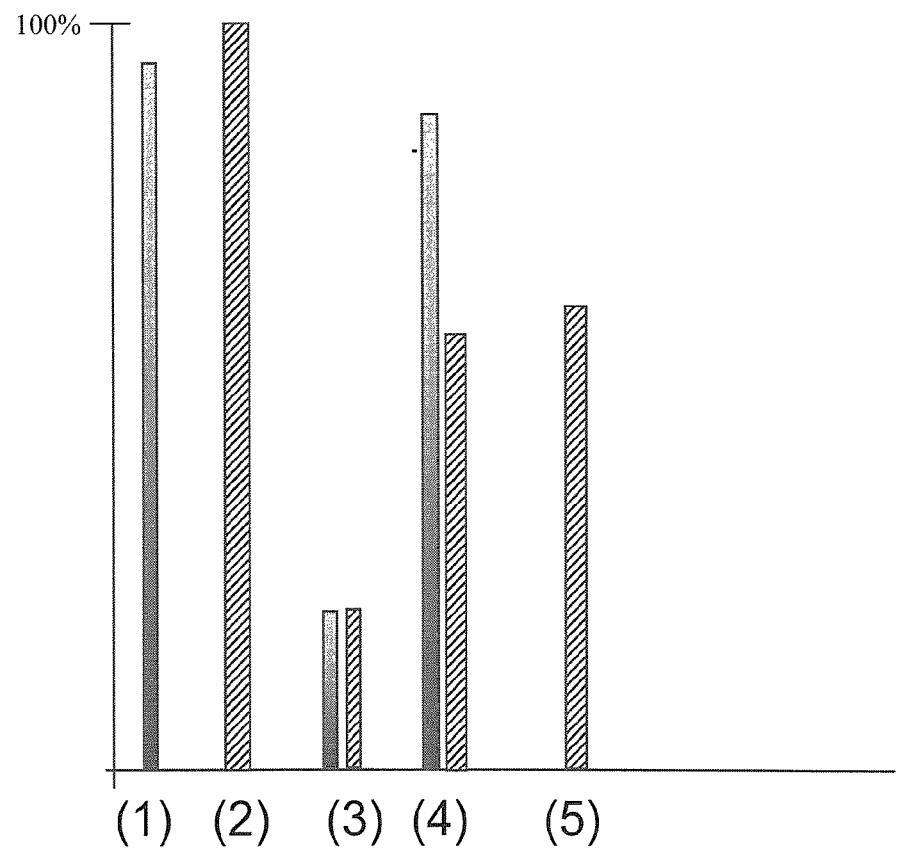
FIG. 14 Resulting aroma (N methylpyrol (N-MP) and acetate aldehyde (AC)) present, after two days, when the aromas are introduced in water and in an ISAMULSION. Note that after 2 days the aromas are stable in an ISAMULSION while they are degraded in water.

FIG. 14 shows the head-space measure of resulting aromas after two days of storage. The Y-axis represents the percentage of aromas remaining, as measured by head space measurement, after the two days of storage. When the aromas are solubilized in the ISAMULSION, there is no visible degradation of aromas while there is a strong degradation of aromas when they are dissolved in water.

Head space measurements are done in the following way. Analyses were performed on an HP 6890 gas chromatograph (GC) equipped with a flame ionization detector (FID) (Agilent, Basel, Switzerland). The GC was coupled to a mass spectrometer (5973 MSD, Agilent) operating in electron ionization (EI) mode et 70 eV. A DB-Wax capillary column (30×0.25 mm, 0.25 micrometer film thickness, J & W Scientific, Folsom, USA) was used for all analyses. The oven was kept at 20° C. for 3 min, raised at 6° C./min to 100° C. and then at 10° C./min to 240° C. Finally, the oven was kept at 240° C. for 10 min. The carrier gas was helium with a flow rate of 1 mL/min. After the equilibrium time (2 h), 2 mL of the head-space sample was injected. Each sample was prepared in triplicate for GC analysis. The following injector parameters were used: syringe, 2.5 mL headspace; sample volume, 2 mL; incubation temperature, 37° C.; agitation speed, 300 rpm; agitation on time, 5 s; agitation off time, 2 s; syringe temperature, 37° C.; fill speed, 100 micro litter/s; pull-up delay, 60 s; injection speed, 1 mL/s; pre-injection delay, 500 ms; post-injection delay, 500 ms; syringe flushing, 1 min. The linearity of the FID signal detected for each odorant in the concentration range of interest was checked by an external calibration curve.

Figure 15:
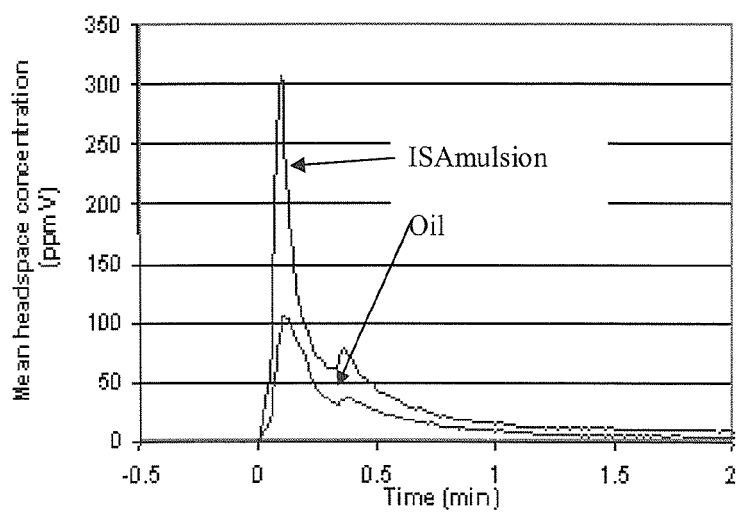
FIG. 15 Result of aroma head-space measurement by Proton Transfer Reaction-Mass Spectrometer (PTR-MS, Ionicon Analytik, Innsbruck, Austria) for an ISAMULSION and a normal emulsion. The aroma release (sum of the mass concentrations detected by PTR-MS) is represented as function of time.

FIG. 15 shows results of aroma head space measurements by Proton Transfer Reaction-Mass Spectrometer (PTR-MS, Ionicon Analytik, Innsbruck, Austria) for an ISAMULSION and a normal oil-in-water emulsion. Notice that a burst release is obtained for the ISAMULSION compared to the normal emulsion. PTRMS was used to follow the on-line aroma release. Full mass spectra from m/z 20 to 160 were recorded in emulsions and ISAMULSIONS. In order to get a more sensitive mass detection, a selection of masses was performed as a function of the good representativity of the molecule(s) identified at each mass. In order to identify the molecules released from the samples, a Tenax trap was fixed at the exhaust of the oven cell outlet for 5 min. The volatiles desorbed from the Tenax trap were then split and analysed by PTR-MS and gaz chromatography-mass spectroscopy (GC-MS).

EXAMPLES

The various embodiments of this invention provide an oil-in-water emulsion in which the dispersed oil droplets exhibit a nano-sized, self-assembled structure of hydrophilic domains due to the presence of a lipophilic additive (LPA). The following examples are illustrative in nature and are not to be construed as limiting the invention, the scope of which is defined by the invention description and appended claims.

Example 1

Generic Examples of an ISAMULSION obtained by homogenization and containing a mineral oil. This example is used to show how an ISAMULSION can be characterized and distinguished from ordinary oil in water emulsions.

Typically 1-5 wt % of a mineral oil, such as tetradecane, was added to 95 wt % water containing already 0.375 wt % of the hydrophilic emulsifier (Tween 80, Merck or Pluronic F127, BASF). 0.5-4 wt % LPA (glycerol monolinoleate, emulsifier TS-PH 039, Danisco, Norway) was then added to the mixture. The total amount of lipophilic molecules (mineral oil+LPA) was 4.625 wt %.

Ultrasonication was then carried out for 20 minutes. The ISAMULSION character of the emulsions was confirmed by cryo-TEM images and SAXS curves such as the ones of FIG. 2 and FIG. 3-4. FIG. 2 and FIG. 3 were obtained from those generic examples with a composition of 2.4 wt % mineral oil (tetradecane)-2.2 wt % LPA-0.375 wt % hydrophilic emulsifier (pluronic F127)-95 wt % water. In addition, corresponding bulk samples (non dispersed samples containing the oil, the LPA, excess water but no hydrophilic emulsifier) were prepared and analysed. The weight ratio oil (tetradecane)/LPA (glycerol monolinoleate) was 1.1/1.0. The mixture oil-LPA-water was heated and mixed with a Vortex until the sample was homogeneous.

Figure 4:
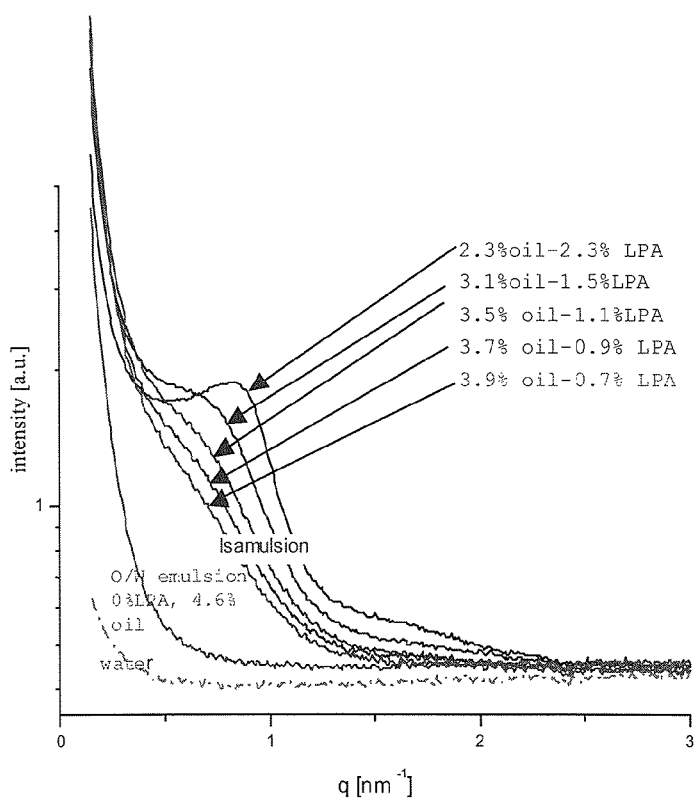
FIG. 4 shows the small angle X-ray scattering (SAXS) pattern of ISAMULSIONS containing various amounts of LPA, i.e., $\alpha$ values ($\alpha=100*LPA/(LPA+OIL)$).

After addition of 0, 5, or 10 wt % water to the oil/LPA mix, the sample was clear indicating that the water was totally solubilized into the oil/LPA mixture and a w/o microemulsion was formed. After addition of higher amounts of water, the sample shows phase separation. It was noted that the samples containing 15 and 20 wt % water show the same SAXS curves as the corresponding ISAMULSION sample (2.4 wt % mineral oil-2.2 wt % LPA-0.375 wt % hydrophilic emulsifier). This demonstrates that ISAMULSION droplets show the same characteristic distance of 7.5 nm as observed in the corresponding bulk phases (see FIG. 3). Moreover, FIG. 4 shows that ISAMULSIONS are formed (e.g. a peak in the SAXS curve is observed) already with relatively low LPA and high oil contents (e.g. 3.9 wt % mineral oil (tetradecane)-0.725 wt % LPA (glycerol monolinoleate), 0.375 wt % hydrophilic emulsifier (pluronic F127)-95% water). However an ISAMULSION is not formed when no LPA is present as shown in FIG. 3 (composition 4.625 wt % oil (tetradecane), 0.375 wt % pluronic F127, 95 wt % water). Also with higher amounts of LPA ($\alpha$ values) (Example of composition: 1.32 wt % tetradecan-3.3 wt % LPA-0.375 wt % Pluronic F127;), an ISAMULSION is formed. The structure is more ordered than observed with a lower $\alpha$ value (LPA content) and shows an inversed micellar cubic arrangement of the hydrophilic domains, as shown by the SAXS curves and cryo-TEM images (FIGS. 5 and 10).

Active elements can be solubilized or dispersed in the ISAMULSIONs as described in example 1 in order to give a new or improved functionality to the product.

Example 2

ISAMULSIONS Using a Triglyceride Oil

This example is used to show how an ISAMULSION from the present invention can be characterized.

0.5-4.5 wt % of soybean oil was mixed with 0.5-4 wt % LPA (Dimodan U/J, Danisco, Denmark). This mixture was added to 95 wt % water containing 0.375% of the hydrophilic emulsifier (Pluronic F127). The total amount of lipophilic molecules (oil+LPA) was 4.625 wt %.

The mixture was sheared using a Polytron (Kinematica, Switzerland) position 5 for five minutes.

The ISAMULSION character of the emulsions was confirmed by cryo-TEM images (FIG. 6a), SAXS (FIG. 7a) and examination of the corresponding bulk samples (as it was done for example 1). FIGS. 6a-7a were obtained from those generic examples with a composition of 1.525 wt % triglyceride oil-3.1 wt % LPA-0.375 wt % hydrophilic emulsifier (pluronic F127)-95 wt % water. No internal structure is observed inside ordinary soybean oil droplets, e.g. in the absence of LPA (FIGS. 6b-7d).

Active elements can be solubilized or dispersed in the ISAMULSION described in example 2 in order to deliver a new or improved functionality to the product.

Example 3

ISAMULSIONS which contain mixtures of several LPAs. This example is used to show how an ISAMULSION can be characterized.

Figure 8:
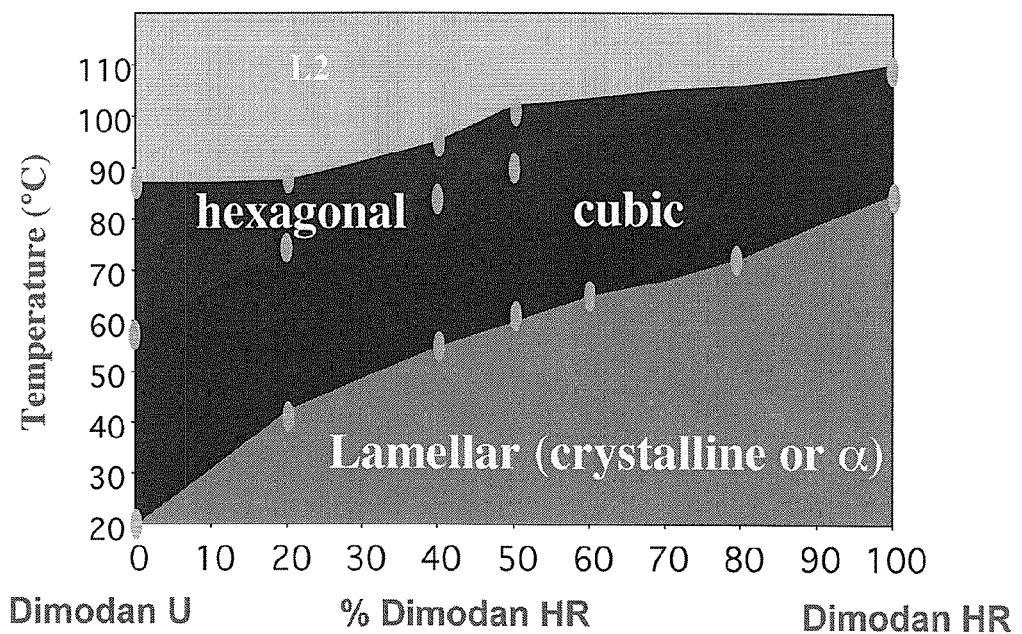
FIG. 8 shows the pseudo binary phase diagram of a saturated-unsaturated monoglyceride mixture in the presence of 20% water.

An ISAMULSION containing a mixture of a saturated and unsaturated monoglyceride:

0-1.8% mineral oil (tetradecane) was added to 0.2-2% LPA. The LPA was a mixture of saturated monoglycerides (Dimodan HR, (saturated monoglycerides containing 90% of glycerol monostearate), Danisco, Denmark) and unsaturated monoglycerides (Dimodan U/J, Danisco, Denmark). The total amount of lipophilic molecules (Oil+LPA) was 3%. The mixture was added to 96.7% water containing 0.3% Tween 80 as hydrophilic emulsifier. Ultrasonication was carried out for 2 minutes. As indicated by the pseudo binary phase diagram of the saturated monoglyceride (Dimodan HR)-unsaturated monoglyceride (Dimodan U/J) mixture obtained at 20% water (FIG. 8), the formation of a stable L2 phase can be obtained at high temperatures after addition of the saturated monoglyceride to the unsaturated monoglyceride sample, indicating that L2 based ISAMULSIONS can be formed at high temperatures. For example, for the compositions 1% tetradecane-1% saturated monoglycerides-1% unsaturated monoglycerides-0.3% Tween 80 and 1% tetradecane, ISAMULSIONS are present and stable at temperatures higher than 60° C.

Figure 11:
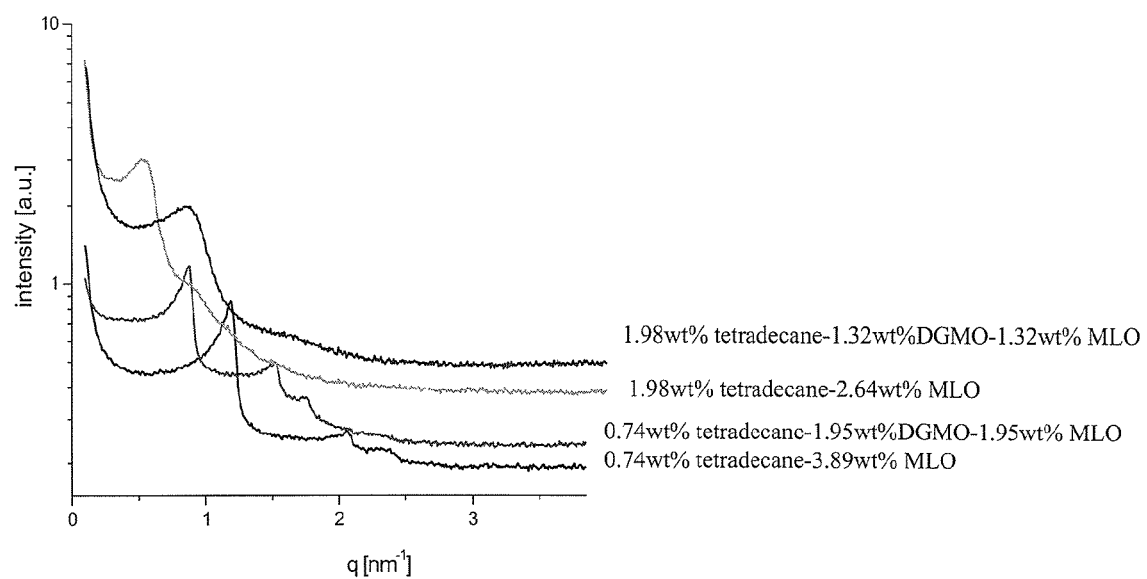
FIG. 11 shows the small angle X-ray scattering (SAXS) patterns of ISAMULSIONS made with oil and a mixture of monolinolein (MLO) and di-glycerol monooleate (DGMO) as the LPA.

Mixtures containing mineral oil (tetradecane), glycerol monolinoleate and diglycerol monooleate:

Tetradecane, monolinolein (MLO), Diglycerol monooleate (DGMO) was added to 95.375 wt % water containing already 0.375 wt % hydrophilic emulsifier (Pluronic F127). Ultrasonication was then carried out for 20 minutes. SAXS reveals the ISAMULSION character of the mixtures (FIG. 11). Compared to ISAMULSIONS made only with glycerol monooleate and without DGMO (FIG. 11), the SAXS peaks are shifted towards higher distances, when DGMO is used, in combination with unsaturated monoglycerides, the hydrophilic domains are getting larger and a higher amount of water can be solubilized in the interior of the droplets. This example demonstrates that mixtures of different LPA's can be used to form the characteristic structure of ISAMULSION oil droplets.

ISAMULSIONS made of with oil and a mixture of a monoglyceride and a phospholipid:

Mineral oil (tetradecane), phosphatidylcholine from soya oil (PC) and diglycerol monooleate (DGMO) were added to 95.375 wt % water containing already 0.375 wt % hydrophilic emulsifier (Pluronic F127). Ultrasonication was then carried out for 20 minutes.

Figure 12:
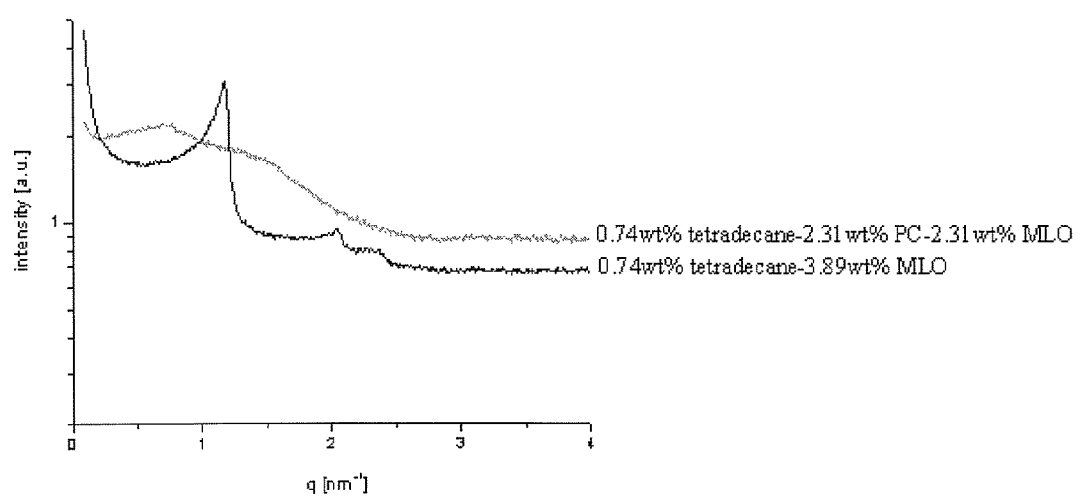
FIG. 12 shows the small angle X-ray scattering (SAXS) patterns of ISAMULSIONS made with oil and a mixture of phospholipids (phospatidylcholine (PC)) and monolinolein (MLO) as the LPA.

SAXS reveals the ISAMULSION character of the mixtures (FIG. 12). Precise composition is given in FIG. 12. This example demonstrates that phospholipids can be used to form the characteristic structure of ISAMULSION oil droplets.

An ISAMULSION using an oil and an emulsifier mixtures, including phospholipids as LPA and a mixture of different oils:

2.2 wt % egg-yolk soybean phosphatidylcholine (Lucas Meyer) was mixed with 2.2 wt % diolein and 0.6 wt % tetradecane. This mixture was added to 94.625 wt % water containing 0.375 wt % of the hydrophilic emulsifier (Pluronic F127). Ultrasonication was then carried out for 40 minutes. An emulsion having the typical ISAMULSION features was formed. The PC can also be mixed with phopshatidylethanolamine (PE) or another Phospholipid in order to obtain the ISAMULSION features. Any combination of different phospholipids and oils is possible to use and generating the typical ISAMULSION features described in this invention.

An ISAMULSION using Phosphoethanolamine (PE) as LPA and oil:

2.2 wt % 1,2-Dioleoyl-sn-Glycero-3-Phosphoethanolamine (AvantiPolar Lipids) was mixed with 0.8 wt % soybean oil. This mixture was added to 96.7 wt % water containing 0.3 wt % of the hydrophilic emulsifier (Pluronic F127). Ultrasonication was then carried out for 40 minutes. An emulsion having the typical ISAMULSION features was formed.

Active elements can be solubilized or dispersed in ISAMULSION described in example 3 in order to give a new or improved functionality to the product.

Example 4

An ISAMULSION Containing a Flavouring Oil for Controlling Flavour Perception 2.3 wt % of an essential oil (R+ limonene) was introduced in 95 wt % water containing already 0.4 wt % hydrophilic emulsifier (Pluronic F127). 2.3 wt % LPA (glycerol monolinoleate) was added to the mixture. Ultrasonication was carried out for 20 minutes. A dispersion was formed.

As in the case of example 1, SAXS reveals the ISAMULSION character of the emulsion. The ISAMULSION is spontaneously formed during the ultrasonication step. This example demonstrates that flavoring oils, such as limonene, can be used as the oil phase for the formation of an ISAMULSION structure.

Example 5

An ISAMULSION Containing Phytosterol Ester and Lycopene with Enhanced Solubility and/or Dispersibility and Bioavailability 1.08 wt % phytosterol ester (ADM)-1.62 wt % Dimodan U/J (LPA)-0.0015 wt % Lyc-O-Mato from Lycored (contains 10 wt % of lycopene) were first heated and mixed with a vortex until the formation of a homogeneous clear solution. This solution was added to 97.1 wt % water in which 0.2 wt % Tween 80 was dissolved. The mixture was treated by ultrasonication for 2 minutes at 80° C. An ISAMULSION was formed having the lycopene solubilized in the interior nanostructure of the oil droplets. This example demonstrates that lipophilic, crystallinic antioxidants can be solubilized in the interior of the structure of ISAMULSION oil droplets giving rise to a homogeneous oil-in-water emulsion.

Example 6

An ISAMULSION Containing Free Phytosterols with Enhanced Solubility or/and Dispersibility and Bioavailability 0.44 wt % free phytosterol (ADM), 1.65 wt % unsaturated monoglyceride (Dimodan U/J, Danisco) and 1.06 wt % soybeen oil are first heated at 120° C. until the phytosterol is dissolved and a solution is formed. 0.2 wt % Tween 80 was dispersed into 96.65 wt % water. The Tween 80 solution was heated until 80° C. and the melted mixture of phytosterol-monoglyceride-soybeen oil was added at 80° C. to the Tween 80 solution. Ultrasonication was carried out at 80° C. for 2 minutes. As a result an ISAMULSION is formed and no crystals are present in the emulsion as confirmed by polarized microscopy. This ISAMULSION can be used to increase bioavailability of phytosterols. If the same process is made, but using a normal emulsion containing even less free phytosterols (0.31 wt % free phytosterol and 2.75 wt %-soybean oil-0.2 wt % Tween 80-96.74 wt % water), large number of crystals are observed after processing.

Example 7

Milk Containing Free Phytosterol in an ISAMULSION to Enhance Solubility and/or Dispersibility and Bioavailability 0.45 wt % free phytosterol (ADM), 1.67 wt % unsaturated monoglyceride (Dimodan U/J, Danisco) and 1.07 wt % soybeen oil are first heated to 120° C. until the phytosterols are dissolved and a solution is formed. 96.81 wt % Low fat milk (Cremo 0 fat milk, Switzerland) was heated to 80° C. The lipid solution was added to the milk and ultrasonication was carried at 80° C. When the milk cooled down, no crystals were observed by polarized light microscopy (FIG. 13b). The milk containing free phytosterol solubilized in an ISAMULSION was then pasteurized at 63° C. for 30 minutes. No crystals were observed for the 4 weeks of storage at 4° C. When the same process is made, but using a normal emulsion (0.39 wt % free phytosterol, 2.37 wt % soybean oil and 97.24 wt % 0 fat milk), a large number of crystals is present after processing (FIG. 13a) and after Pasteurization.

Example 8

Milk Containing Free Phytosterol and Milk Fat to Enhance Solubility and/or Dispersibility and Bioavailability 0.42 wt % free phytosterols (ADM), 1.59 wt % unsaturated monoglyceride (Dimodan U/J or Dimodan MO90, Danisco) and 1.02 wt % milk fat are first heated to 120° C. until the phytosterols are dissolved and a solution is formed. Low fat milk (Cremo 0 fat milk from Coop, Switzerland) was heated to 80° C. The lipid solution was added to 96.97 wt % milk and ultrasonication was carried at 80° C. No sterol crystals were observed by polarized light microscopy after processing and having let cooled the milk to room temperature.

Example 9

An ISAMULSION Containing Lutein to Enhance Solubility and/or Dispersibility and Bioavailability 0.001 g lutein, 0.4 g soya oil and 0.6 g Dimodan U/J were heated until a homogeneous and clear solution is formed. 0.2 g Tween 80 was dissolved into 19 g water heated to 80° C. The lipidic mixture heated to 80° C. was added to the Tween solution at 80° C. Ultrasonication was carried for 2 minutes. An ISAMULSION was formed and no crystals were detected by polarized light microscopy when the sample was cooled down to room temperature.

Example 10

An ISAMULSION Containing Free Phytosterols and Phytosterol Esters as an Oil to Enhance Solubility and/or Dispersibility and Bioavailability 0.21 wt % free phytosterol (ADM), 0.79 wt % unsaturated monoglyceride (Dimodan U/J or Dimodan M090, Danisco) and 0.52 wt % phytosterol ester (Danisco) were first heated to 120° C. until the free phytosterol is dissolved and a solution is formed. 0.2 wt % Tween 80 was dispersed into 98.28 wt % water. The Tween 80 solution was heated to 80° C. and the lipid mixture was added at 80° C. to the Tween 80 solution. Ultrasonication was carried at 80° C. for 2 minutes. As a result an ISAMULSION is formed and no crystals are present as confirmed by polarized light microscopy.

Example 11

A Milk Containing Free Phytosterol and Phytosterol Ester as an Oil to Enhance Solubility and/or Dispersibility and Bioavailability 0.21 wt % free phytosterol (ADM), 0.79 wt % unsaturated monoglyceride (Dimodan U/J or Dimodan M090, Danisco) and 0.52 wt % phytosterol ester (Danisco) were first heated at 120° C. until the free phytosterol is dissolved and a solution is formed. 98.48 wt % Low fat milk (Cremo 0 fat, Switzerland) was heated to 80° C. The lipid solution was added to the milk and ultrasonication was carried out at 80° C. No sterol crystals were observed by polarized light microscopy after processing and having let cooled the milk down to room temperature.

Example 12

An ISAMULSION Containing Ascorbyl Palmitate to Enhance Solubility and/or Dispersibility and Increased Efficiency 0.01 wt % ascorbyl palmitate and 0.594 wt % Dimodan U/j were mixed and heated until ascorbyl palmitate is dissolved. 0.3996 wt % soya oil was then added to the homogeneous solution. The lipidic solution obtained was added at 80° C. to 0.1 wt % sodium caseinate introduced into 98.9 wt % water at 80° C. Ultrasonication was used for 2 minutes at 80° C. After the process, an ISAMULSION is obtained. When cooling down to room temperature no crystals were observed by polarized light microscopy.

Example 13

An ISAMULSION Containing Polyunsaturated Fatty Acids (PUFAs,) Vitamin E and Vitamin C to Protect PUFA from Oxidation 2 wt % Fish oil (SOFINOL SA, Manno Switzerland) was mixed with 2.625 Dimodan U/J and 0.001 wt % Vitamin E (Covi-Ox T70 mixed tocopherols, Cognis Cincinnati USA) until an homogeneous solution is obtained. The lipid solution was then added to 0.375 wt % Tween 80 introduced into 95 wt % water. Ultrasonication was used for 2 minutes. After the process, an ISAMULSION is obtained. 0.001 wt % Vitamin C (Fluka, Buchs Switzerland) is then added to the ISAMULSION.

Example 14

ISAmulsions Containing Ascorbyl Palmitate in a Large Amount 0.2% ascorbyl palmitate (Danisco, Denmark) is mixed with 2% Dimodan U and heated at 60° C. to obtain a solution. 1% of soya been oil is then added to the lipid mixture and then introduced in 96.3% water containing 0.5% Tween 80. Ultrasonication was carried out at 60° C. for five minutes. An ISAMULSION is obtained which contains solubilized ascorbyl palmitate and no crystal is observed by polarized light microscopy.

Example 15

Milk Containing PUFA Protected from Oxidation 0.05 g ascorbyl palmitate was dissolved at 60° C. in 5 g Dimodan U. The mixture formed by ascorbyl palmitate and Dimodan U was dissolved in 95 g fish oil forming the lipophilic solution. 0.6 g of the lipophilic solution was added to 20 g skimmed milk (cremo 0 fat milk Switzerland). Ultrasonication was used for obtaining an ISAMULSION.

Example 16

ISAMULSIONs which Contain Polyunsaturated Fatty Acids (PUFA), Vitamin E and Ascorbyl Palmitate and Used to Protect PUFA From Oxidation 0.002 wt % ascorbyl palmitate and 2.625 wt % Dimodam U were mixed and heated until acorbyl palmitate was dissolved. 2 wt % fish oil (SOFINOL SA, Manno Switzerland) and 0.001 wt % Vitamin E (Covi-Ox T70 mixed tocopherols, Cognis Cincinnati USA) was added to the homogeneous solution.

The lipidic solution obtained is added to 0.375 wt % Tween 80 introduced into 95 wt % water. Ultrasonication was used for 2 minutes. After the process, an ISAMULSION is obtained in which the fish oil is significantly protected from oxidation.

Example 17

An ISAMULSION which Contains Free Phytosterol, Polyunsaturated Fatty Acids (PUFAs), Vitamin E and sscorbyl Palmitate and Used to Deliver PUFAs and to Prevent Cholesterol Absorption 0.002 wt % ascorbyl palmitate and 2.625 wt % Dimodam U were mixed and heated until acorbyl palmitate was dissolved. 1.45 wt % fish oil (SOFINOL SA, Manno Switzerland), 0.55% free phytosterol and 0.001 wt % Vitamin E (Covi-Ox T70 mixed tocopherols, Cognis Cincinnati USA) were added to the homogeneous solution. The lipidic mixture was heated till obtaining an homogeneous solution. The lipidic solution obtained is added at 80° C. to 0.375 wt % Tween 80 introduced into 95 wt % water preheated at 80° C. Ultrasonication was used for 2 minutes. After the process, an ISAMULSION is obtained and no crystals are observed by polarized microscopy.

If the same is done using a normal emulsion, by replacing Dimodan U with the oil, such as soybean oil (final composition: 0.002 wt % ascorbyl palmitate, 2.625 wt % soya oil, 1.45 wt % fish oil, 0.55% free phytosterol, 0.001 wt % Vitamin E, 0.375 wt % Tween 80, 95% water), or fish oil etc, the free phytosterol is not solubilized and a large number of large crystals are observed by microscopy.

Example 18

An ISAMULSION to Prevent Reaction between N-Methylpyrol and Acetate Aldehyde to Increase Chemical Stability 3 wt % dimodan U/J, 2 wt % soya oil and 0.5 wt % Tween 80 were added to 94.5 wt % water. 10 minutes of ultrasonication was used to produce an ISAMULSION. 200 ppm of N-Methyl pyrol (N-MP) and 200 ppm of Acetate aldehyde (AC) was added to the ISAMULSION. In another experiment, 200 ppm of N-Methyl pyrol (N-MP) and 200 ppm of Acetate aldehyde (AC) were added directly into water.

FIG. 14 shows the remaining concentration of aroma after 2 days in the ISAMULSION and in water. It clearly demonstrates that reactivity between Ac and N-MP is strongly reduced in an ISAMULSION compared to water.

Example 19

An ISAMULSION to Prevent Reaction between Sulfites and Propanal to Increase Chemical Stability 3 wt % dimodan U/J, 2 wt % soya oil and 0.5 wt % Tween 80 were added to 94.5 wt % water. 10 minutes of ultrasonication was used to produce an ISAMULSION. 200 ppm of propanal and 200 ppm of sulfites were put into the ISAMULSION. In another experiment, 200 ppm of sulfites and 200 ppm propanal were added directly to the water phase. As in example 18, after two days, the reaction was significantly reduced when the ISAMULSION was present compared to the situation where the aromas were present in a normal aqueous phase.

Example 20

An ISAMULSION Containing Gamma-Oryzanol to Enhance Solubility and Bioavailability 0.05 g gamma-Oryzanol, 0.27 g Dimodan U/J, 0.18 g soya oil were heated until an homogeneous solution is formed and let cooled to 80° C. 0.1 g Tween 80 was dissolved in 9.4 g water and heated to 80° C. The two solutions were mixed together and ultrasonication was carried out for 2 minutes. Once the sample has cooled down to room temperature, no crystals were observed by polarized microscopy. If the same process is applied to a normal emulsion (composition: 0.5 wt % gamma-Oryzanol, 4.5 wt % soya oil, 1 wt % Tween 80 and 94 wt % water), a large number of crystals were evidenced after the sample has cooled down to room temperature by polarized light microscopy.

Example 21

An ISAMULSION to Deliver Mouth Coating and Mouth Feel Functionality 1.507 g sunflower oil was heated and mixed with 1 g Dimodan U/J until a homogeneous solution is formed. The lipidic solution is added to 47.5 g water containing 0.05 g sodium caseinate. Ultrasonication was carried out for two minutes. Mouth coating was obtained for the ISAMULSION formed. If an emulsion is made (composition 47.1 g water, 0.4 g sodium caseinate, 2.5 g sunflower oil) the same way, less mouth coating was obtained.

Example 22

A Concentrated ISAMULSION with High Loading of Vitamin E Acetate 1 wt % of sodium caseinate was dispersed into 94 wt % water. 3% vitamin E-acetate was mixed with 2% Dimodan U/J to form a homogeneous solution. The lipidic solution was added to the caseinate solution and ultrasonication was applied for 10 minutes, until a concentrated ISAMULSION is formed.

This concentrated ISAMULSION can be easily added to any food or cosmetic product to enrich or fortify the product with vitamin E acetate. The vitamin E acetate is homogeneously distributed through the product.

Example 23

An ISAMULSION to Solubilize Vitamin E and Ascorbyl Palmitate to Enhance Chemical Stability of Vitamin E and to Increase Bioavailability and Efficiency of Vitamin E 0.01 wt % ascorbyl palmitate and 0.595 wt % Dimodan U/j were mixed and heated until the acorbyl palmitate is dissolved. 0.3986 wt % vitamin E was then added to the homogeneous solution. The lipidic solution obtained was added to 0.1 wt % sodium caseinate introduced into 98.9 wt % water. Ultrasonication was used for 2 minutes. After the process, an ISAMULSION is obtained which protects vitamin E against oxidation and thereby increase the efficiency of vitamin E.

Example 24

An ISAMULSION Enriched with Natural Active Elements by Extraction

A mixture of 320 g of tomato concentrate and 80 g of oil, i.e. a mixture of soybean oil and DIMODAN U/J in a ratio of 35/65 was heated to 45° C. and mixed with a kitchen mixer during 1 minute. After centrifugation of the mixture with a Sorvall centrifuge during 1 h and 5000 RPM at 40° C., 60 g of the oil phase was recovered. HPLC analysis of this oil phase revealed a lycopene content of 4 mg/100 g extract. When increasing the extraction temperature to 60° C. and mixing the mixture for 10 minutes, after centrifugation, the lycopene content in the oily phase was increased to 20 mg/100 g lycopene. 5 g of the lipidic phase obtained (containing Dimodan U/J, soybeen oil and extracted active elements including lycopene) was added into 94.5 g water containing 0.5 g Tween 80. Ultrasonication was carried out for 5 minutes. An ISAMULSUION enriched with bioavailable natural active elements (extracted from raw tomatoes), including lycopene, is obtained.

Example 25

A Stable Beverage which Contains a Lipophilic Vitamin Cocktail 10.0 g of Eficacia (CNI, France) is added to 979 g Vittel (Nestlé, France) water and dissolved with a magnetic stirrer. 80 mg of vitamin D (DSM, Switzerland), 18 mg of vitamin K (DSM, Switzerland), 7.2 g of vitamin E (DSM, Switzerland), 160 mg of vitamin A (DSM, Switzerland) were dissolved into 3.6 g Dimodan U at 50° C.

The Dimodan U/Vitamins solution was added to the Eficacia solution and a rotor/stator homogenizer (Polytron) was used for five minutes. The solution was further homogenized using a Rannie homogenizer. The first 100 ml were left out and the remaining 900 ml were recovered in a bottle. The formed ISAMULSION is physically stable (no phase separation, creaming, ring formation).

If the same is done by replacing Dimodan U with a standard oil like soybeen oil an ordinary emulsion is obtained. The physical stability of this emulsion is much lower than the stability of the respective ISAMULSION.

The concentrated emulsion is diluted with normal or aromatized water to obtain a lipophilic enriched vitamin beverage.

Example 26

An Aromatized Beverage 10.0 g of Eficacia (CNI, France) is added to 980 g Vittel (Nestlé, France) water and dissolved with a magnetic stirrer. 6.3 g orange essential oil was added to 3.6 g Dimodan U at 50° C.

The Dimodan U/essential oil solution was added to the Vittel and a rotor/stator homogenizer (Polytron) was used for five minutes. The solution was further homogenized using a Rannie homogenizer. The first 100 ml were left out and the remaining 900 ml were recovered in a bottle. The so formed ISAMULSION is physically stable (no phase separation or creaming and ring formation).

If the same is done by replacing Dimodan U by a standard oil like soybean oil (10 g Eficacia, 3.6 g Dimodan U, 3.6 g orange essential oil), an emulsion is obtained which has only a low physical stability (creaming, ring formation after some days of storage) than obtained in the ISAMULSION.

The emulsion concentrate can be diluted with water to obtain a lipophilic enriched vitamin beverage.

Example 27

Refreshing Drinks Containing Mint Oil 0.13 wt % mint oil and 0.0032 wt % Dimodan U were mixed and heated till forming an homogeneous solution. 0.13 wt % Eficacia (CNI, France) were added to 99.74% water and dispersed using a magnetic agitator. The lipid mixture was added to the Eficacia solution. A stable emulsion (no creaming, ring formation) is obtained using a Polytron homogenizer for 10 minutes. The emulsion can be diluted to obtain a refreshing drink.

Example 28

A Drink Giving a Sustained Refreshing Sensation 0.26 wt % mint oil and 0.039 wt % Dimodan U were mixed and heated till forming an homogeneous solution. 0.26 wt % Eficacia (CNI, France) were added to 99.44% water and dispersed using a magnetic agitator. The lipid mixture was added to the Eficacia solution. A stable emulsion was obtained using a Polytron homogenizer for 10 minutes. The emulsion can be diluted to obtain a ready-to-use drink which has a long lasting refreshing effect.

Example 29

ISAMULSION Containing Vitamin E Protected From Oxidation 0.05% ascorbyl palmitate (Danisco, Denmark) was dissolved at 60° C. in 0.6% Dimodan U. 0.4 wt % d-α tocopherol (Acros organics, New Jersey, USA) was mixed with the Dimodan U/ascorbyl palmitate mixture. The obtained lipidic solution was added to 98.75% water containing 0.2% sodium caseinate (Emmi, Switzerland). Ultrasonication was carried out for 2 minutes to obtain a dispersion of vitamin E, with the vitamin E protected from oxidation.

The ISAMULSIONS prepared according to the above mentioned examples can be used as such or as an additive.

Having now fully described the invention, it will be understood by those of ordinary skill in the art that the same can be performed within a wide and equivalent range of conditions, formulations and other parameters without affecting the scope of the invention or any embodiment thereof.

The invention claimed is:

1. A method for colour modulation, increasing browning, controlling chemical reaction yield or controlling Maillard reaction yield due to the formation of the nano-sized self-assembled structure inside the oil droplets comprising the step of using an oil-in-water emulsion having oil droplets of a diameter ranging from 5 nm to hundreds of micrometers exhibit a nano-sized self-assembled structurization with liquid hydrophilic domains having a diameter size of 0.5 to 200 nm, due to the presence of a lipophilic additive and the oilin-water emulsion contains an active element comprising between 0.00001 and 79% of the total composition.

2. A method for extracting active elements from any kind of raw materials or products to enrich an oil-in-water emulsion due to the formation of a nano-sized self-assembled structure inside oil droplets comprising the step of using an oil-in-water emulsion having oil droplets of a diameter ranging from 5 nm to hundreds of micrometers exhibit a nano-sized self-assembled structurization with liquid hydrophilic domains having a diameter size of 0.5 to 200 nm, due to the presence of a lipophilic additive and the oil-in-water emulsion contains an active element comprising between 0.00001 and 79% of the total composition.

3. A method for extracting active elements, from any kind of raw materials or products, in the mouth, during consumption or digestion in order to control their release for health or sensory benefits due to the formation of the nano-sized self-assembled structure inside the oil droplets comprising the step of using an oil-in-water emulsion having oil droplets of a diameter ranging from 5 nm to hundreds of micrometers exhibit a nano-sized self-assembled structurization with liquid hydrophilic domains having a diameter size of 0.5 to 200 nm, due to the presence of a lipophilic additive and the oil-in-water emulsion contains an active element comprising between 0.00001 and 79% of the total composition.

* * * * *